United States Patent
Lang et al.

(10) Patent No.: US 11,801,294 B2
(45) Date of Patent: Oct. 31, 2023

(54) METHOD OF ENHANCING INNATE IMMUNE RESPONSES AGAINST A TUMOR COMPRISING ADMINISTERING LYMPHOCYTIC CHORIOMENINGITIS VIRUS (LCMV)

(71) Applicant: ABALOS THERAPEUTICS GMBH, Essen (DE)

(72) Inventors: Karl Sebastian Lang, Essen (DE); Halime Kalkavan, Memphis, TN (US)

(73) Assignee: ABALOS THERAPEUTICS GMBH, Essen (DE)

( * ) Notice: Subject to any disclaimer, the term of this patent is extended or adjusted under 35 U.S.C. 154(b) by 0 days.

(21) Appl. No.: 16/267,095

(22) Filed: Feb. 4, 2019

(65) Prior Publication Data

US 2019/0151436 A1    May 23, 2019

Related U.S. Application Data

(62) Division of application No. 15/567,343, filed as application No. PCT/EP2016/058347 on Apr. 15, 2016, now abandoned.

(30) Foreign Application Priority Data

Apr. 17, 2015   (DE) .......................... 102015207036.0

(51) Int. Cl.
| | | |
|---|---|---|
| *A61K 39/12* | (2006.01) | |
| *A61K 35/76* | (2015.01) | |
| *A61K 35/768* | (2015.01) | |
| *C12N 7/00* | (2006.01) | |
| *A61K 39/00* | (2006.01) | |
| *A61P 35/00* | (2006.01) | |

(52) U.S. Cl.
CPC .............. *A61K 39/12* (2013.01); *A61K 35/76* (2013.01); *A61K 35/768* (2013.01); *C12N 7/00* (2013.01); *A61K 2039/5254* (2013.01); *A61K 2039/585* (2013.01); *A61P 35/00* (2018.01); *C12N 2760/10011* (2013.01); *C12N 2760/10021* (2013.01); *C12N 2760/10032* (2013.01); *C12N 2760/10033* (2013.01)

(58) Field of Classification Search
CPC ...... A61K 35/76; A61K 35/768; A61K 39/12; A61K 2039/5254; C12N 2760/10011; C12N 2760/10021; C12N 2760/10033; C12N 2760/10032
See application file for complete search history.

(56) References Cited

U.S. PATENT DOCUMENTS

2008/0124308 A1   5/2008  Laer et al.
2018/0117137 A1   5/2018  Kalkavan et al.

FOREIGN PATENT DOCUMENTS

| CN | 101641092 A | 2/2010 |
| CN | 101918565 A | 12/2010 |
| DE | 102015207036 A1 | 10/2016 |
| WO | 2006008074 A1 | 1/2006 |
| WO | 2008147474 A2 | 12/2008 |
| WO | 2009083210 A1 | 7/2009 |
| WO | 2011056993 A1 | 5/2011 |
| WO | 2016166285 A1 | 10/2016 |

OTHER PUBLICATIONS

Molomut, N., and M. Padnos, Dec. 1965, Inhibition of transplantable and spontaneous murine tumors by the M-P virus, Nature 208(6014):948-950.*
Sevilla, N., and J. C. de la Torre, 2006, Arenavirus diversity and evolution: quasispecies in vivo, Curr. Topics Microbiol. Immunol. 299:315-335.*
Flatz, L., et al., Mar. 2006, Recovery of an arenavirus entirely from RNA polymerase I/II-driven cDNA, Proc. Natl. Acad. Sci. 103(12):4663-4668.*
Ciurea, A., et al., Oct. 1999, Persistence of lymphocytic choriomeningitis virus at very low levels in immune mice, Proc. Natl. Acad. Sci. 96(21):11964-11969.*
Koma, T., et al., 2013, Innate immune response to arenaviral infection: a focus on the highly pathogenic new world hemorrhagic arenaviruses, J. Mol. Biol. 425:4893-4903.*
Lukashevich, I. S., et al., 2004, LCMV-mediated hepatitis in rhesus macaques: WE but not ARM strain activates hepatocytes and induces liver regeneration, Arch. Virol. 149:2319-2336.*
Bergthaler, A., et al., Dec. 2010, Viral replicative capacity is the primary determinant of lymphocytic choriomeningitis virus persistence and immunosuppression, PNAS 107(50):21641-21646.*
Snell, L. M., et al., Aug. 2017, Type I interferon in chronic virus infection and cancer, Trends Immunol. 38(8):542-557.*
Rankin, E. B., et al., Nov./Dec. 2003, An essential role of Th1 responses and interferon gamma in infection-mediated suppression of neoplastic growth, Cancer Biology & Therapy, 2(6):687-693.*
Lukashevich, I. S., et al., 2004, LCMV-mediated hepatitis in rhesus macaques: WE but not ARM strain activate hepatocytes and induces liver regeneration, Arch. Virol. 149:2319-2336.*
Wang, Y., et al., Jun. 2012, Timing and magnitude of type I interferon responses by distinct sensors impact CD8 T cell exhaustion and chronic viral infection, Cell Host Microbe 11:631-642.*
Richter, K., et al., 2013, Reversal of chronic to resolved infection by IL-10 blockade is LCMV strain dependent, Eur. J. Immunol. 43:649-654.*
Ruggeri, B. A., et al., 2014, Animal models of disease: Pre-clinical animal models of cancer and their applications and utility in drug discovery, Biochem. Pharmacol. 87:150-161.*

(Continued)

*Primary Examiner* — Jeffrey S Parkin
(74) *Attorney, Agent, or Firm* — Acuity Law Group, PC; Michael A. Whittaker

(57) ABSTRACT

The invention relates to arenaviruses for use in the treatment and/or prevention of tumors and also a method for preparing arenaviruses with (improved) tumor-regressive properties.

13 Claims, 9 Drawing Sheets

Specification includes a Sequence Listing.

(56) References Cited

OTHER PUBLICATIONS

Wartha, K., et al., 2014, Fit-for purpose use of mouse models to improve predictivity of cancer therapeutics evaluation, Pharmacol. Therap. 142:351-361.*
Chulpanova, D. S., et al., 2020, Mouse tumor models for advanced cancer immunotherapy, Int. J. Mol. Sci. 21:1-15.*
Cheng et al., Generation of Recombinant Arenavirus for Vaccine Development in FDA-Approved Vero Cells. J Vis Exp. Aug. 1, 2013; (78): e50662 (9 pages).
Ciurea et al., Persistence of lymphocytic choriomeningitis virus at very low levels in immune mice. Proc Natl Acad Sci U S A. Oct. 12, 1999;96(21):11964-11969.
International Preliminary Report on Patentability issued in PCT/EP2016/058347 dated Oct. 17, 2017—incl Engl lang transl (17 pages total).
International Search Report issued in PCT/EP2016/058347 dated Jul. 1, 2016—incl Engl lang transl (24 pages total).
Emonet et al., Rescue from Cloned cDNAs and In Vivo Characterization of Recombinant Pathogenic Romero and Live-Attenuated Candid #1 Strains of Junin Virus, the Causative Agent of Argentine Hemorrhagic Fever Disease. J Virol. Feb. 2011;85(4):1473-1483.
Flatz et al., Development of replication-defective lymphocytic choriomeningitis virus vectors for the induction of potent CD8+ T cell immunity. Nat Med. Mar. 2010;16(3):339-345.
Goni et al., Genomic features of attenuated Junin virus vaccine strain candidate. Virus Genes. Feb. 2006;32(1):37-41.
Goni et al., Molecular analysis of the virulence attenuation process in Junin virus vaccine genealogy. Virus Genes. Jun. 2010;40(3):320-328.
Groseth et al., Tacaribe Virus but Not Junin Virus Infection Induces Cytokine Release from Primary Human Monocytes and Macrophages. PLoS Negl Trop Dis. May 10, 2011;5(5):e1137.
Iwasaki et al., General Molecular Strategy for Development of Arenavirus Live-Attenuated Vaccines. J Virol. Dec. 2015;89(23):12166-12177.
Kalkavan et al., Spatiotemporally restricted arenavirus replication induces immune surveillance and type I interferon-dependent tumour regression. Nat Commun. Mar. 1, 2017;8:14447.
Kelly and Russell, History of Oncolytic Viruses: Genesis to Genetic Engineering. Mol Ther. Apr. 2007;15(4):651-659.
Kohler et al., Enhanced tumor susceptibility of immunocompetent mice infected with lymphocytic choriomeningitis virus. Cancer Immunol Immunother. 1990;32(2):117-124.
Koma et al., Innate Immune Response to Arenaviral Infection: A Focus on the Highly Pathogenic New World Hemorrhagic Arenaviruses. J Mol Biol. Dec. 13, 2013;425(24):4893-4903.
Miletic et al., Efficient Transduction and Therapy of Malignant Glioma by Lentiviral Vectors Pseudotyped with LCMV Glycoproleins. Mol Ther May 2005;11(Supp.1):S31.
Miletic et al., Selective Transduction of Malignant Glioma by Lentiviral Vectors Pseudotyped with Lymphocytic Choriomeningitis Virus Glycoproteins. Hum GeneTher. Nov. 2004;15(11):1091-1100.
Molomut and Padnos, Inhibition of Transplantable and Spontaneous Murine Tumours by the M-P Virus. Nature. Dec. 4, 1965;208(5014):948-950.
Oldenburg et al., Differences in tropism and pH dependence for glycoproteins from the Clade B1 arenaviruses: Implications for receptor usage and pathogenicity. Virology. Jul. 20, 2007;364(1):132-139.
Reiserova et al., Identification of MaTu-MX Agent as a New Strain of Lymphocytic Choriomeningitis Virus (LCMV) and Serological Indication of Horizontal Spread of LCMV in Human Population. Virology. Apr. 25, 1999;257(1):73-83.
Schadler et al., Immunosurveillance by Antiangiogenesis: Tumor Growth Arrest by T Cell-Derived Thrombospondin-1. Cancer Res. Apr. 15, 2014;74(8):2171-2181.
Southam and Moore, Clinical Studies of Viruses as Anlineoplastic Agents, with Particular Reference to Egypt 101 Virus. Cancer. Sep. 1952;5(5):1025-1034.

Webb et al., The Treatment of 18 Cases of Malignant Disease with an Arenavirus. Clin Oncol. Jun. 1975;1(2):157-169.
Zapata and Salvato, Arenavirus Variations Due to Host-Specific Adaptation. Viruses. Jan. 17, 2013;5(1):241-278.
Zhang et al., Pseudotyping Lentiviral Vectors with Lymphocytic Choriomeningitis Virus Glycoproteins for Transduction Uf Dendritic Cells and In Vivo Immunization. Hum Gene Ther Methods. Dec. 2014;25(6):328-338.
Office Action issued in EP 16717129.7 dated Oct. 21, 2019—incl Engl lang transl (13 pages total).
Office Action issued in EP 16717129.7 dated Dec. 20, 2019—incl Engl lang transl (9 pages total).
Office Action issued in JP 2018/-505536 dated Feb. 6, 2020—incl Engl lang transl (22 pages total).
Honke et al., Usp18 Driven Enforced Viral Replication in Dendritic Cells Contributes to Break of Immunological Tolerance in Autoimmune Diabetes. PLoS Pathog. Oct. 2013;9(10):e1003650 Oct. 2013 (11 pages).
Ochsenbein et al., Roles of tumour localization, second signals and cross priming in cytotoxic T-cell induction. Nature , Jun. 28, 2001;411 (6841):1058-1064 (plus erratum—1 page)—10 pages total.
Borrow et al., Inhibition of the Type 1 Interferon Anti viral Response During Arenavirus Infection. Viruses Nov. 2010;2(11):2443-2480.
Lexikon der Biologie, transgene Organismen', Jan. 1, 1996, accessed online at: https://www.spektrum.de/lexikon/biologie/transgene-organismen/67248—incl Engl lang transl (2 pages total).
Macal et al., Plasmacytoid dendritic cells are productively infected and activated through TLR-7 early after arenavirus infection. Cell Host Microbe. Jun. 14, 2012;11(6):617-30.
Office Action issued in EP 16717129.7 dated Sep. 2, 2020—incl Engl lang transl (15 pages total).
Carnec et al. "Lassa Virus Nucleoprotein Mutants Generated by Reverse Genetics Induce a Robust Type I Interferon Response in Human Dendritic Cells and Macrophages", Journal of Virology, Nov. 2011, p. 12093-12097.
Kalkavan et al. "Spatiotemporally restricted arenavirus replication induces immune surveillance and type I interferon-dependent tumour regression", Nature Communications | 8:14447 | DOI: 10.1038/ncomms14447 |www.nature.com/naturecommunications, Mar. 2017, pp. 1-14.
Martinez-Sobrido et al. "Inhibition of the Type I Interferon Response by the Nucleoprotein of the Prototypic Arenavirus Lymphocytic Choriomeningitis Virus", Journal of Virology, Sep. 2006, p. 9192-9199.
Wang et al. "Timing and Magnitude of Type I Interferon Responses by Distinct Sensors Impact CD8 T Cell Exhaustion and Chronic Viral Infection", Cell Host & Microbe ,11, 631-642, Jun. 14, 2012.
Webb et al. "The treatment of 18 cases of malignant disease with an arenavirus", Clinical Oncology, 1975, 1:157-1969.
Office Action issued by the CNIPA in Chinese Patent Application No. 201680030624.5 dated Oct. 9, 2020—incl Engl lang transl (8 pages total).
A431 Xenograft Model, https://altogenlabs.com/xenograft-models/melanoma-xenograft/a431-xenograft-model/, retrieved Sep. 9, 2022 (6 pages).
A549—A model for non-small cell lung canger, https://drugdevelopment.labcorp.com/industry-solutions/oncology/precl . . . , retrieved Sep. 9, 2022 (6 pages).
Everything You Need to Know about A549 Cells, https://www.synthego.com/a549-cells, retrieved Sep. 9, 2022 (7 pages).
A549 Xenograft Model, https://altogenlabs.com/xenograft-models/lung-cancer-xenograft/a549-xenograft-model/, retrieved Sep. 9, 2022 (7 pages).
HeLa Xenograft Model, https://altogenlabs.com/xenograft-models/other-bladder-cervical/hela-xenograft-model/, retrieved Sep. 9, 2022 (7 pages).
Buschow et al., "In Vivo Imaging of an Inducible Oncogenic Tumor Antigen Visualizes Tumor Progression and Predicts CTL Tolerance", J Immunol. Mar. 15, 2010;184(6):2930-8. doi: 10.4049/jimmunol.0900893. Epub Feb. 8, 2010.

(56) References Cited

OTHER PUBLICATIONS

Macal et al., Plasmacytoid Dendritic Cells Are Productively Infected and Activated through TLR-7 Eady after Arenavirus Infection. Cell Host Microbe. Jun. 14, 2012;11(6):617-630.

Office Action issued by the JPO in Japanese application No. 2021-088871 dated Jul. 5, 2022—incl Engl lang transl (6 pages total).

Office Action issued by the CNIPA in Chinese Patent Application No. 201680030624.5 dated Aug. 31, 2021—incl Engl lang transl (10 pages total).

\* cited by examiner

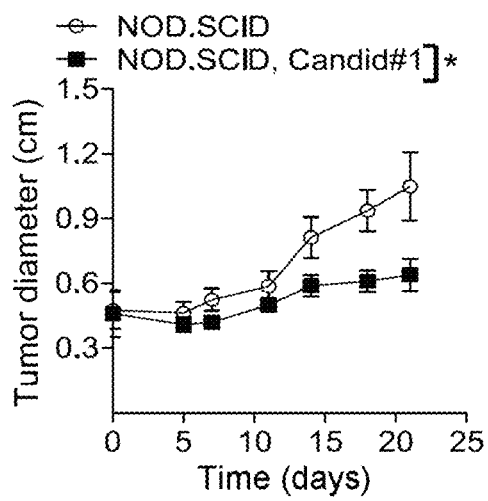
Figure 13
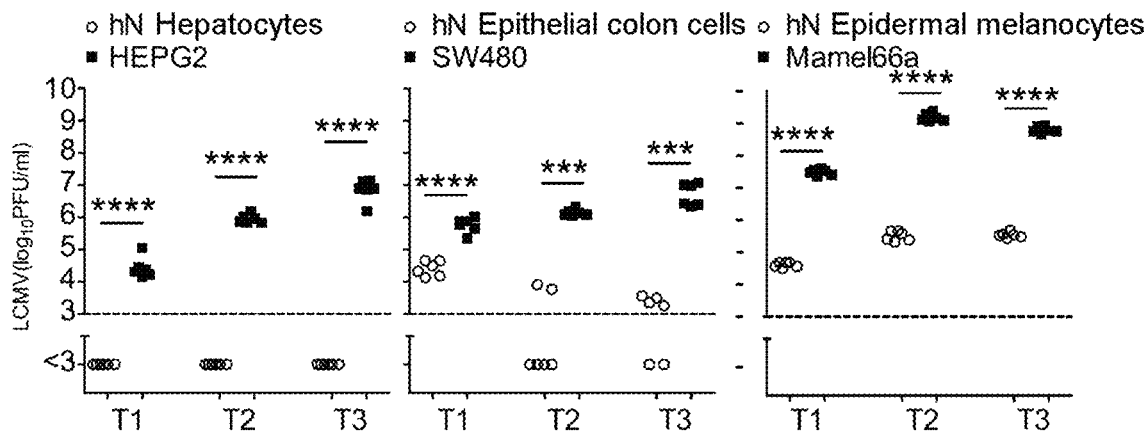
Figure 14
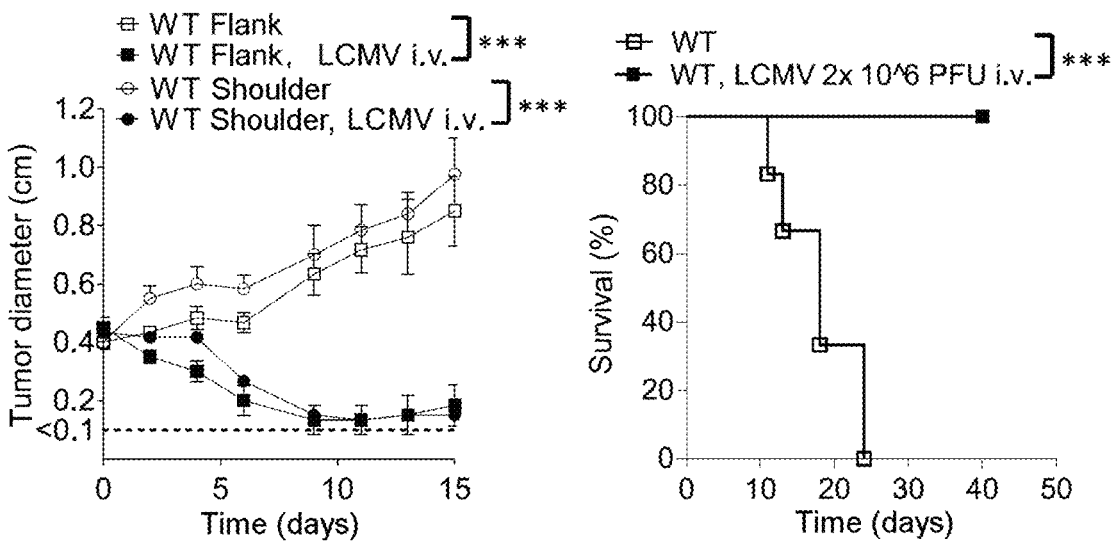
Figure 15A
Figure 15B

SEQUENCE LISTING

```
<160> NUMBER OF SEQ ID NOS: 6

<210> SEQ ID NO 1
<211> LENGTH: 3413
<212> TYPE: RNA
<213> ORGANISM: Junin virus
<220> FEATURE:
<223> OTHER INFORMATION: Junin virus strain Candid-1 segment S -
      AY746353 - virusesM> ssrna negative-strand virusesM> arenavir
      idaeM> arenavirusM> new world arenaviruses

<400> SEQUENCE: 1
gtgcagtaag gggatcctag gcgattttgg ttacgctata attgtaactg ttttctgttt      60
ggacaacatc aaaaacatcc attgcacaat ggggcagttc attagcttca tgcaagaaat     120
accaaccttt ttgcaggagg ctctgaacat tgctcttgtt gcagtcagtc tcattgccat     180
```

```
cattaagggt atagtgaact tgtacaaaag tggtttattc caattctttg tattcctagc    240
gcttgcagga agatcctgca cagaagaagc tttcaaaatc ggactgcaca ctgagttcca    300
gactgtgtcc ttctcaatgg tgggtctctt ttccaacaat ccacatgacc tacctttgtt    360
gtgtacctta aacaagagcc atctttacat taagggggc aatgcttcat ttcagatcag     420
ctttgatgat attgcagtat tgttgccaca gtatgatgtt ataatacaac atccagcaga    480
tatgagctgg tgttccaaaa gtgatgatca aatttggttg tctcagtggt tcatgaatgc    540
tgtggggcat gattggcatc tagacccacc atttctgtgt aggaaccgtg caaagacaga    600
aggcttcatc tttcaagtca cacctccaa gactggtgtc aatggaaatt atgctaagaa     660
gtttaagact ggcatgcatc atttatatag agaatatcct gacccttgct tgaatggcaa    720
actgtgctta atgaaggcac aacctaccag ttggcctctc caatgtccac tcgaccacgt    780
taacacatta cacttcctta caagaggtaa aaacattcaa cttccaagga ggtccttgaa    840
agcattcttc tcctggtctt tgacagactc atccggcaag gatacccctg gaggctattg    900
tctagaagag tggatgctcg tagcagccaa aatgaagtgt tttggcaata ctgctgtagc    960
aaaatgcaat ttgaatcatg actctgaatt ctgtgacatg ttgaggctct ttgattacaa   1020
caaaaatgct atcaaaaccc taatgatga actaagaaa caagtaaatc tgatggggca     1080
gacaatcaat gccctgatat ctgacaattt attgatgaaa aacaaaatta gggaactgat   1140
gagtgtccct tactgcaatt acacaaaatt ttggtatgtc aaccacacac tttcaggaca   1200
acactcatta ccaaggtgct ggttaataaa aaacaacagc tatttgaaca tctctgactt   1260
ccgtaatgac tggatattag aaagtgactt cttaatttct gaaatgctaa gcaaagagta   1320
ttcggacagg cagggtaaaa ctcctttgac tttagttgac atctgtattt ggagcacagt   1380
attcttcaca gcgtcactct tccttcactt ggtgggtata ccctcccaca gacacatcag   1440
gggcgaagca tgccctttgc cacacaggtt gaacagcttg ggtggttgca gatgtggtaa   1500
gtaccccaat ctaaagaaac caacagtttg gcgtagagga cactaagacc tcctgagggt   1560
ccccaccagc ccgggcactg cccgggctgg tgtggccccc cagtccgcgg cctggccgcg   1620
gactggggag gcactgctta cagtgcatag gctgccttcg ggaggaacag caagctcggt   1680
ggtaatagag gtgtaggttc ctcctcatag agcttcccat ctagcactga ctgaaacatt   1740
atgcagtcta gcagagcaca gtgtggttca ctggaggcca acttgaaggg agtatccttt   1800
tccctctttt tcttattgac aaccactcca ttgtgatatt tgcataagtg accatatttc   1860
tcccagacct gttgatcaaa ctgcctggct tgttcagatg tgagcttaac atcaaccagt   1920
ttaagatctc ttcttccatg gaggtcaaac aacttcctga tgtcatcgga tccttgagta   1980
gtcacaacca tgtctggagg cagcaagccg atcacgtaac taagaactcc tggcattgca   2040
tcttctatgt ccttcattaa gatgccgtga gagtgtctgc taccattttt aaaccctttc   2100
tcatcatgtg gttttctgaa gcagtgaatg tactgcttac ctgcaggttg aataatgcc    2160 atctcaacag ggtcagtggc tggtccttca atgtcgagcc aaagggtgtt ggtggggtcg   2220
agtttcccca ctgcctctct gatgacagct tcttgtatct ctgtcaagtt agccaatctc   2280
aaattctgac cgttttttc cggctgtcta ggaccagcaa ctggtttcct tgtcagatca    2340
atacttgtgt tgtcccatga cctgcctgtg atttgtgatc tagaaccaat ataaggccaa   2400
ccatcgccag aaagacaaag tttgtacaaa aggttttcat aaggatttct attgcctggt   2460
ttctcatcaa taaacatgcc ttctcttcgt ttaacctgaa tggttgattt tatgagggaa   2520
```

| | |
|---|---:|
| gagaagttttt ctggggtgac tctgattgtt tccaacatgt ttccaccatc aagaatagat | 2580 |
| gctccagcct ttactgcagc tgaaagactg aagttgtaac cagaaatatt gatggagctt | 2640 |
| tcatctttag tcacaatctg aaggcagtca tgttcctgag tcagtctgtc aaggtcactt | 2700 |
| aagtttggat acttcacagt gtatagaagc ccaagtgagg ttaaagcttg tatgacactg | 2760 |
| ttcattgtct cacctccttg aacagtcatg catgcaattg tcaatgcagg aacagagcca | 2820 |
| aactgattgt ttagctttga agggtcttta acatcccata tcctcaccac accatttccc | 2880 |
| ccagtccctt gctgttgaaa tcccagtgtt ctcaatatct ctgatctttt agcaagttgt | 2940 |
| gactgggaca agttacccat gtaaaccccc tgagagcctg tctctgctct tcttatcttg | 3000 |
| tttttttaatt tctcaaggtc agacgccaac tccatcagtt catccctccc cagatctccc | 3060 |
| accttgaaaa ctgtgtttcg ttgaacactc tcatggaca tgagtctgtc aacctcttta | 3120 |
| ttcaggtccc tcaacttgtt gaggtcttct tccccctttt tagtctttct gagtgcccgc | 3180 |
| tgcacctgtg ccacttggtt gaagtcgatg ctgtcagcaa ttagcttggc gtccttcaaa | 3240 |
| acatctgact tgacagtctg agtgaattgg ctcaaacctc tccttaagga ctgagtccat | 3300 |
| ctaaagcttg gaacctcctt ggagtgtgcc atgccagaag ttctggtgat tttgatctag | 3360 |
| aatagagttg ctcagtgaaa gtgttagaca ctatgcctag gatccactgt gcg | 3413 |

<210> SEQ ID NO 2
<211> LENGTH: 7114
<212> TYPE: RNA
<213> ORGANISM: Junin virus
<220> FEATURE:
<223> OTHER INFORMATION: Junin virus strain Candid #1 segment L - AY819707 - virusesM> ssrna negative-strand virusesM> arenaviridaeM> arenavirusM> new world arenaviruses

<400> SEQUENCE: 2

| | |
|---|---:|
| cgcacagtgg atcctaggcg taacttcatc attaaaatct cagattctgc tctgagtgtg | 60 |
| acttactgcg aagaggcaga caaatgggca actgcaacgg ggcatccaag tctaaccagc | 120 |
| cagactcctc aagagccaca cagccagccg cagaatttag gagggtagct cacagcagtc | 180 |
| tatatggtag atataactgt aagtgctgct ggtttgctga taccaatttg ataacctgta | 240 |
| atgatcacta cctttgttta aggtgccatc agggtatgtt aaggaattca gatctctgca | 300 |
| atatctgctg gaagccctg cccaccacaa tcacagtacc ggtggagcca acagcaccac | 360 |
| caccataggc agactgcaca gggtcagacc cgacccccg ggggcccccc atggggaccc | 420 |
| cccgtggggg aaccccgggg gtgatgcgcc attagtcaat gtctttgatc tcgactttgt | 480 |
| gcttcagtgg cctgcatgtc acccctttca atctgaactg cccttgggga tctgatatca | 540 |
| gcaggtcatt taaagatctg ctgaatgcca ccttgaaatt tgagaattcc aaccagtcac | 600 |
| caaatttatc aagtgaacgg atcaactgct ctttgtgtag atcataaacg aggacaaagt | 660 |
| cctcttgctg aaataatatt gtttgtgatg ttgttttag ataaggccat agttggctta | 720 |
| ataaggtttc cacactatca atgtcctcta gtgctccaat tgccttgact atgacatccc | 780 |
| cagacaactc aactctatat gttgacaacc tttcattacc tctgtaaaag ataccctctt | 840 |
| tcaagacaag aggttctcct gggttatctg gcccaatgag gtcatatgca tacttgttac | 900 |
| ttagttcaga ataaaagtca ccaaagttga acttaacatg gctcagaata ttgtcatcat | 960 |
| ttgtcgcagc gtagcctgca tcaataaaca agccagctag gtcaaagctc tcatggcctg | 1020 |
| tgaacaatgg taggctagcg ataaccatgt caccatccaa caatgagtgg cttccctcag | 1080 |
| acccagaaac acattgactc attgcatcca cattcagctc taattcaggg gtaccgacat | 1140 |

```
catccactcc tagtgaactg acaatggtgt aactgtacac catctttctt ctaagtttaa   1200
attttgtcga aactcgtgtg tgttctactt gaatgatcaa ttttagtttc acagcttctt   1260
ggcaagcaac attgcgcaac acagtgtgca ggtccatcat gtcttcctga ggcaacaagg   1320
agatgttgtc aacagagaca ccctcaagga aaaccttgat attatcaaag ctagaaacta   1380
cataacccat tgcaatgtct tcaacaaaca ttgctcttga tactttatta ttcctaactg   1440
acaaggtaaa atctgtgagt tcagctagat ctacttgact gtcatcttct agatctagaa   1500
cttcattgaa ccaaaagaag gatttgagac acgatgttga catgactagt gggtttatca   1560
tcgaagataa gacaacttgc accatgaagt tcctgcaaac ttgctgtggg ctgatgccaa   1620
cttcccaatt tgtatactct gactgtctaa catgggctga agcgcaatca ctctgtttca   1680
caatataaac attattatct cttactttca ataagtgact tataatccct aagttttcat   1740
tcatcatgtc tagagccaca cagacatcta gaaacttgag tcttccacta tccaaagatc   1800
tgttcacttg aagatcattc ataaagggtg ccaaatgttc ttcaaatagt ttggggtaat   1860
ttcttcgtat agaatgcaat acatggttca tgcctaattg gtcttctatc tgtcgtactg   1920
ctttgggttt aacagcccag aagaaattct tattacataa gaccagaggg gcctgtggac   1980
tcttaatagc aaaaaacacc cactccccta actcacaggc atttgtcagc accaaagaga   2040
agtaatccca caaaattggt ttagaaaatt ggttaacttc tttaagtgat ttttgacagt   2100
aaataacttt aggctttctc tcacaaattc cacaaagaca tggcattatt cgagtaaata   2160
tgtcctttat atacagaaat ccgcctttac catccctaac acacttactc cccatactct   2220
tacaaaaccc aatgaagcct gaggcaacag aagactgaaa tgcagatttg ttgattgact   2280
ctgccaagat cttcttcacg cctttttgtga aatttcttga cagcctggac tgtattgtcc   2340
ttatcaatgt tggcatctct tctttctcta acactcttcg acttgtcatg agtttggtcc   2400
tcaagaccaa cctcaagtcc ccaaagctcg ctaaattgac ccatctgtag tctagagttt   2460
gtctgatttc atcttcacta cacccggcat attgcaggaa tccggataaa gcctcatccc   2520
ctcccctgct tatcaagttg ataaggtttt cctcaaagat tttgcctctc ttaatgtcat   2580
tgaacacttt cctcgcgcag ttccttataa acattgtctc cttatcatca gaaaaaatag   2640
cttcaatttt cctctgtaga cggtaccctc tagacccatc aacccagtct ttgacatctt   2700
gttcttcaat agctccaaac ggagtctctc tgtatccaga gtatctaatc aattggttga   2760
ctctaatgga aatctttgac actatatgag tgctaacccc attagcaata cattgatcac   2820
aaattgtgtc tatggtctct gacagttgtg ttggagtttt acacttaacg ttgtgtagag   2880
cagcagacac aaacttggtg agtaaaggag tctcttcacc catgacaaaa atcttgact   2940 taaactcagc aacaaaagtt cctatcacac tctttgggct gataaacttg tttaatttag   3000
aagataagaa ttcatggaag cacaccattt ccagcagttc tgtcctgtct gaaacttttt   3060
catcactaag gcaaggaatt tttataaggc taacctggtc atcgctggag gtataagtga   3120
caggtatcac atcatacaat aagtcaagtg cataacacag aaattgttca gtaattagcc   3180
catataaatc tgatgtgttg tgcaagattc cctggcccat gtccaagaca gacattatat   3240
ggctggggac ctggtccctt gactgcagat actggtgaaa aaactcttca ccaacactag   3300
tacagtcaca acccattaaa cctaaagatc tcttcaattt ccctacacag taggcttctg   3360
caacattaat tggaacttca acgacccttat gaagatgcca tttgagaatg ttcattactg   3420
gttcaagatt caccttttgtt ctatctctgg gattcttcaa ttctaatgtg tacaaaaaag   3480
```

```
aaaggaaaag tgctgggctc atagttggtc cccatttgga gtggtcatat gaacaggaca    3540
agtcaccatt gttaacagcc attttcatat cacagattgc acgttcgaat tccttttctg    3600
aattcaagca tgtgtatttc attgaactac ccacagcttc tgagaagtct tcaactaacc    3660
tggtcatcag cttagtgttg aggtctccca catacagttc tctatttgag ccaacctgct    3720
ccttataact tagtccaaat ttcaagttcc ctgtatttga gctgatgctt gtgaactctg    3780
taggagagtc gtctgaatag aaacataaat tccgtagggc tgcatttgta aaataacttt    3840
tgtctagctt atcagcaatg gcttcagaat tgctttccct ggtactaagc cgaacctcat    3900
cctttagtct cagaacttca ctggaaaagc ccaatctaga tctacttcta tgctcataac    3960
tacccaattt ctgatcataa tgtccttgaa ttaaaagata cttgaagcat tcaaagaatt    4020
catcttcttg gtaggctatt gttgtcaaat ttttaataa caaacccaaa gggcagatgt    4080
cctgcggtgc ttcaagaaaa taagtcaatt taaatggaga tagataaaca gcatcacata    4140
actctttata cacatcagac ctgagcacat ctggatcaaa atccttcacc tcatgcattg    4200
acacctctgc tttaatctct ctcaacactc caaaaggggc ccacaatgac tcaagagact    4260
ctcgctcatc aacagatgga tttttgatt tcaacttggt gatctcaact tttgtcccct    4320
cactattagc catcttggct agtgtcattt gtacgtcatt tctaatacc tcaaaggccc    4380 ttacttgatc ctctgttaaa ctctcataca tcactgataa ttcttcttga ttggttctgg    4440
ttcttgaacc ggtgctcaca agacctgtta gattttttaa tattaagtag tccatggaat    4500
caggatcaag attatacctg cctttgtttt taaacctctc agccatagta gaaacgcatg    4560
ttgaaacaag tttctcctta tcataaacag aaagaatatt tccaagttcg tcgagcttgg    4620
ggattaccac acttttattg cttgacagat ccagagctgt gctagtgatg ttaggcctgt    4680
agggattgct tttcagttca cctgtaactt taagtcttcc tctattgaag agagaaatgc    4740
agaaggacaa aatctcttta cacactcctg gaatttgagt atctgaggaa gtcttagcct    4800
ctttggaaaa gaatctgtcc aatcctctta tcatggtgtc ctcttgttcc agtgttagac    4860
tcccacttag agggggtttt acaacaacac aatcaaactt gactttgggc tcaataaact    4920
tctcaaaaca cttgatttga tctgtcaggc gatcaggtgt ctctttggtt accaagtgac    4980
acagataact aacatttaat agatatttaa accttcttgc aaagtaaaga tctgcatctt    5040 cccttcacc caaaattgtc tggaaaagtt ccacagccat cctctgaatc agcacctctg    5100
atccagacat gcagtcgacc cttaactttg acatcaaatc cacatgatgg atttgatttg    5160
catatgccat caagaaatat cttagacctt gtaaaaatgt ctggttcctt ttggaagggg    5220
aacagagtac agctaacact aacaatctta atattggcct tgtcattgtc atgagttcgt    5280
ggctaaaatc caaccagctg gtcatttcct cacacatttc aattaacaca tcctccgaaa    5340 ataggcag gaaaaatctc tttggatcac agtaaaaaga gccttgttct tccaataccc    5400
cattgatgga tagatagata gaatagcacc ttgacttctc acctgttttt tggtaaaaca    5460
agagaccaaa tgtattcttt gtcagatgaa atctttgtac ataacactct cttagtctaa    5520
cattcccaaa atatctagaa tactctcttt cattgattaa caatcgggag gaaaatgatg    5580
tcttcatcga gttgaccaat gcaagggaaa tggaggacaa aatcctaaat aatttcttct    5640
gctcaccttc cactaagctg ctgaatggct gatgtctaca gattttctca aattccttgt    5700
taatagtata tctcatcact ggtctgtcag aaacaagtgc ctgagctaaa atcatcaagc    5760
tatccatatc agggtgtttt attagttttt ccagctgtga ccagagatct tgatgagagt    5820
tcttcaatgt tctggaacac gcttgaaccc acttggggct ggtcatcaat ttcttcctta    5880
```

| | |
|---|---|
| ttagtttaat cgcctccaga atatctagaa gtctgtcatt gactaacatt aacatttgtc | 5940 |
| caacaactat tcccgcattt cttaaccttä caattgcatc atcatgcgtt ttgaaaagat | 6000 |
| cacaaagtaa attgagtaaa actaagtcca gaaacagtaa agtgtttctc ctggtgttga | 6060 |
| aaacttttag acctttcact tgttacaca cggaaagggc ttgaagataa cacctctcta | 6120 |
| cagcatcaat agatatagaa ttctcatctg actggctttc catgttgact tcatctattg | 6180 |
| gatgcaatgc gatagagtag actacatcca tcaacttgtt tgcacaaaaa gggcagctgg | 6240 |
| gcacatcact gtctttgtgg cttcctaata agatcaagtc atttataagc ttagactttt | 6300 |
| gtgaaaattt gaatttcccc aactgcttgt caaaaatctc cttcttaaac caaaaccttä | 6360 |
| actttatgag ttcttctctt atgacagatt ctctaatgtc tcctctaacc ccaacaaaga | 6420 |
| gggattcatt taacctctca tcataaccca aagaattcct tttcaagcat tcgatgtttt | 6480 |
| ctaatcccaa gctctggttt tttgtgttgg acaaactatg gatcaatcgc tggtattctt | 6540 |
| gttcttcaat attaatctct tgcataaatt ttgatttctt taggatgtcg atcagcaacc | 6600 |
| accgaactct ttcaacaacc caatcagcaa ggaatctatt gctgtagcta gatctgccat | 6660 |
| caaccacagg aaccaacgta atccctgccc ttagtaggtc ggactttagg tttaagagct | 6720 |
| ttgacatgtc actcttccat tttctctcaa actcatcagg attgaccctä acaaaggttt | 6780 |
| ccaataggat gagtgttttc cctgtgagtt tgaagccatc cggaatgact tttgaaggg | 6840 |
| tgggacatag tatgccatag tcagacagga tcacatcaac aaacttctga tctgaattga | 6900 |
| tctgacaggc gtgtgcctca caggactcaa gctctactaa acttgacaga agtttgaacc | 6960 |
| cttccaacaa cagagagctg gggtgatgtt gagataaaaa gatgtccctt tggtatgcta | 7020 |
| gctcctgtct ttctggaaaa tgctttctaa taaggctttt tatttcattt actgattcct | 7080 |
| ccatgctcaa gtgccgccta ggatccactg tgcg | 7114 |

<210> SEQ ID NO 3
<211> LENGTH: 3410
<212> TYPE: RNA
<213> ORGANISM: Junin mammarenavirus
<220> FEATURE:
<223> OTHER INFORMATION: Junin virus strain Candid #1 segment S,
      completesequence.-ACCESSION FJ969442-VERSION FJ969442.1-GI:26
      4665554 - Viruses; ssRNA viruses; ssRNA negative-strand viruses;
      Arenaviridae; Mammarenavirus.

<400> SEQUENCE: 3

| | |
|---|---|
| cgcacagtgg atcctaggcg attttggtta cgctataatt gtaactgttt tctgtttgga | 60 |
| caacatcaaa aacatccatt gcacaatggg gcagttcatt agcttcatgc aagaaatacc | 120 |
| aaccttttg caggaggctc tgaacattgc tcttgttgca gtcagtctca ttgccatcat | 180 |
| taagggtgta gtgaacctgt acaaaagtgg tttgttccaa ttctttgtat tcctagcact | 240 |
| cgcaggaaga tcctgcacag aagaagcttt taaaatcgga ctgcacacag agttccagac | 300 |
| tgtgtccttc tcaatggtgg gtctcttttc caacaatcca catgacctgc ctctgttgtg | 360 |
| taccttaaac aagagccatc tttacattaa gggggggcaat gcttcatttc agatcagctt | 420 |
| tgatgatatt gcagtattgt tgccacagta tgatgttata atacaacatc cagcagatat | 480 |
| gagctggtgt tccaaaagtg atgatcaaat ttggttgtct cagtggttca tgaatgctgt | 540 |
| gggacatgat tggcatctag acccaccatt tctgtgtagg aaccgtgcaa agacagaagg | 600 |
| cttcatcttt caagtcaaca cctccaagac tggtgtcaat ggaaattatg ctaagaagtt | 660 |
| taagactggc atgcatcatt tatatagaga atatcctgac ccttgcttga atggcaaact | 720 |

```
gtgcttaatg aaggcacaac ctaccagttg gcctctccaa tgtccactcg accacgttaa      780
cacattacac ttccttacaa gaggtaaaaa cattcaactt ccaaggaggt ccttgaaagc      840
attcttctcc tggtctttga cagactcatc cggcaaggat acccctggag gctattgtct     900
agaagagtgg atgctcgttg cagccaaaat gaagtgtttt ggcaatactg ctgtagcaaa     960
atgcaatctg aatcatgact ctgaattctg tgacatgctg aggcttttg attacaacaa     1020 aaatgctatc aaaaccttaa atgatgaaac taagaaacaa gtaaatctga tgggacagac     1080
aatcaatgcg ctgatatctg acaatttatt gatgaaaaac aaaattaggg aactgatgag     1140
tgtcccttac tgcaattaca caaaattttg gtatgtcaac cacacacttt caggacaaca     1200
ctcattacca aggtgctggt aataaaaaaa caacagctat ttgaacatct ctgacttccg     1260
taatgactgg atattagaaa gtgacttctt aatttctgaa atgctaagca aagagtattc     1320
ggacaggcag ggtaaaactc ctttgacttt agttgacatc tgtatttgga gcacagtatt     1380
cttcacagcg tcactcttcc ttcacttggt gggtataccc tcccacagac acatcagggg     1440
cgaagcatgc cctttgccac acaggttgaa cagcttgggt ggttgcagat gtggtaagta     1500
ccccaatcta agaaaccaa cagtttggcg tagaggacac taagacctcc tgagggtccc     1560
caccagcccg ggcactgccc gggctggtgt ggccccccag tccgcggcct ggccgcggac     1620
tggggaggca ctgcttacag tgcataggct gccttcggga ggaacagcaa gctcggtggt     1680
aatagaggtg taggttcctc ctcatagagc ttcccatcta gcactgactg aaacattatg     1740
cagtctagca gagcacagtg tggttcactg gaggccaact tgaagggagt atcctttcc     1800 ctcttttct tattgacaac cactccattg tgatatttgc ataagtgacc atatttctcc     1860
cagacctgtt gatcaaactg cctggcttgt tcagatgtga gcttaacatc aaccagttta     1920
agatctcttc ttccatggag gtcaaacaac ttcctgatgt catcggatcc ttgagtagtc     1980
acaaccatgt ctggaggcag caagccgatc acgtaactaa gaactcctgg cattgcatct     2040
tctatgtctt tcattaagat gccgtgagag tgtctgctac catttttaaa ccctttctca     2100
tcatgtggtt ttctgaagca gtgaatatac tgcttacctg caggctggaa caacgccatc     2160
tcaacagggt cagtagctgg tccttcaatg tcgagccaaa gggtattggt ggggtcgagt     2220
ttccccactg cctctctgat gacagcttct tgtatctctg tcaagttagc caatctcaaa     2280
ttctgaccgt tcttttccgg ttgtctaggt ccagcaactg gtttccttgt cagatcaata     2340
cttgtgttgt cccatgacct gcctatgatt tgtgatctgg aaccaatata aggccaacca     2400
tcgccagaaa ggcaaagttt gtacagaagg ttttcataag ggtttctatt gcctggtttc     2460
tcatcaataa acatgccttc tcttcgttta acctgaatgg ttgatttat gagggaagaa     2520 aagttatctg gggtgactct gattgtctcc aacatatttc caccatcaag aatggatgca     2580
ccagccttta ctgcagctga aagactaaag ttgtagccag aaatgttgat ggagctttca     2640
tccttagtca caatctggag gcagtcatgt tcctgagtca atctgtcaag gtcactcaag     2700
tttggatact tcacagtgta tagaagccca agagaggtta aagcctgtat gacactgttc     2760
attgtctcac ctccttgaac agtcatgcat gcaattgtca atgcaggaac agaaccaaac     2820
tgattgttaa gttttgaagg atctttaaca tcccataccc tcaccacacc atttccccca     2880
gttccttgct gttgaaatcc cagtgttctc aatatctctg atctcttggc cagttgtgat     2940
tgagacaagt tacccatgta aaccccttga gagcctgtct ctgctcttct aatcttgttt     3000
tttaatttct caaggtcaga cgccaactcc atcagttcat ccctcccag atctcccacc     3060
```

| | |
|---|---|
| ttgaaaactg tgtttcgttg aacactcctc atggacatga gtctgtcaac ctctttattc | 3120 |
| aggtccctca acttattgag gtcttcttcc cccctttag tctttctgag tgcccgctgc | 3180 |
| acctgtgcct cttggttgaa gtcaatgctg tcagcaatta gcttggcatc cttcagaaca | 3240 |
| tccgacttga cagtctgagt aaattgactc aaacctctcc ttaaggactg agtccatcta | 3300 |
| aagcttggaa cctctttgga gtgtgccatg ccagaagttc tggtgatttt gatctagaat | 3360 |
| agagttgctc agtgaaagtg ttagacacta tgcctaggat ccactgtgcg | 3410 |

<210> SEQ ID NO 4
<211> LENGTH: 7114
<212> TYPE: RNA
<213> ORGANISM: Junin mammarenavirus
<220> FEATURE:
<223> OTHER INFORMATION: Junin virus strain Candid #1 segment L,
complete sequence.-ACCESSION AY819707-VERSION AY819707.2-GI:2
27957900-Viruses; ssRNA viruses; ssRNA negative-strand viruses;
Arenaviridae; Mammarenavirus.

<400> SEQUENCE: 4

| | |
|---|---|
| cgcacagtgg atcctaggcg taacttcatc attaaaatct cagattctgc tctgagtgtg | 60 |
| acttactgcg aagaggcaga caaatgggca actgcaacgg ggcatccaag tctaaccagc | 120 |
| cagactcctc aagagccaca cagccagccg cagaatttag gagggtagct cacagcagtc | 180 |
| tatatggtag atataactgt aagtgctgct ggtttgctga taccaatttg ataacctgta | 240 |
| atgatcacta cctttgttta aggtgccatc agggtatgtt aaggaattca gatctctgca | 300 |
| atatctgctg gaagcccctg cccaccacaa tcacagtacc ggtggagcca acagcaccac | 360 |
| caccataggc agactgcaca gggtcagacc cgaccccccg ggggccccc atggggaccc | 420 |
| cccgtggggg aaccccgggg gtgatgcgcc attagtcaat gtctttgatc tcgactttgt | 480 |
| gcttcagtgg cctgcatgtc accctttca atctgaactg cccttgggga tctgatatca | 540 |
| gcaggtcatt taaagatctg ctgaatgcca ccttgaaatt tgagaattcc aaccagtcac | 600 |
| caaatttatc aagtgaacgg atcaactgct cttttgtgtag atcataaacg aggacaaagt | 660 |
| cctcttgctg aaataatatt gtttgtgatg ttgttttag ataaggccat agttggctta | 720 |
| ataaggtttc cacactatca atgtcctcta gtgctccaat tgccttgact atgacatccc | 780 |
| cagacaactc aactctatat gttgacaacc tttcattacc tctgtaaaag atacccctctt | 840 |
| tcaagacaag aggttctcct gggttatctg gcccaatgag gtcatatgca tacttgttac | 900 |
| ttagttcaga ataaaagtca ccaaagttga acttaacatg gctcagaata ttgtcatcat | 960 |
| ttgtcgcagc gtagcctgca tcaataaaca agccagctag gtcaaagctc tcatggcctg | 1020 |
| tgaacaatgg taggctagcg ataaccagtg caccatccaa caatgagtgg cttccctcag | 1080 |
| acccagaaac acattgactc attgcatcca cattcagctc taattcaggg gtaccgacat | 1140 |
| catccactcc tagtgaactg acaatggtgt aactgtacac catctttctt ctaagtttaa | 1200 |
| attttgtcga aactcgtgtg tgttctactt gaatgatcaa ttttagttc acagcttctt | 1260 |
| ggcaagcaac attgcgcaac acagtgtgca ggtccatcat gtcttcctga ggcaacaagg | 1320 |
| agatgttgtc aacagagaca ccctcaagga aaaccttgat attatcaaag ctagaaacta | 1380 |
| cataaccat tgcaatgtct tcaacaaaca ttgctcttga tactttatta ttcctaactg | 1440 |
| acaaggtaaa atctgtgagt tcagctagat ctacttgact gtcatcttct agatctagaa | 1500 |
| cttcattgaa ccaaaagaag gatttgagac acgatgttga catgactagt gggtttatca | 1560 |
| tcgaagataa gacaacttgc accatgaagt tcctgcaaac ttgctgtggg ctgatgccaa | 1620 |

```
cttcccaatt tgtatactct gactgtctaa catgggctga agcgcaatca ctctgtttca    1680
caatataaac attattatct cttactttca ataagtgact tataatccct aagttttcat    1740
tcatcatgtc tagagccaca cagacatcta gaaacttgag tcttccacta tccaaagatc    1800
tgttcacttg aagatcattc ataaagggtg ccaaatgttc ttcaaatagt ttggggtaat    1860
ttcttcgtat agaatgcaat acatggttca tgcctaattg gtcttctatc tgtcgtactg    1920
ctttgggttt aacagcccag aagaaattct tattacataa gaccagaggg gcctgtggac    1980
tcttaatagc aaaaaacacc cactcccta actcacaggc atttgtcagc accaaagaga    2040
agtaatccca caaaattggt ttagaaaatt ggttaacttc tttaagtgat ttttgacagt    2100
aaataacttt aggctttctc tcacaaattc cacaaagaca tggcattatt cgagtaaata    2160
tgtcctttat atacagaaat ccgcctttac catccctaac acacttactc cccatactct    2220
tacaaaaccc aatgaagcct gaggcaacag aagactgaaa tgcagatttg ttgattgact    2280
ctgccaagat cttcttcacg cctttttgtga aatttcttga cagcctggac tgtattgtcc    2340
ttatcaatgt tggcatctct tctttctcta acactcttcg acttgtcatg agtttggtcc    2400
tcaagaccaa cctcaagtcc ccaaagctcg ctaaattgac ccatctgtag tctagagttt    2460
gtctgatttc atcttcacta cacccggcat attgcaggaa tccggataaa gcctcatccc    2520
ctcccctgct tatcaagttg ataaggtttt cctcaaagat tttgcctctc ttaatgtcat    2580
tgaacacttt cctcgcgcag ttccttataa acattgtctc cttatcatca gaaaaaatag    2640
cttcaatttt cctctgtaga cggtaccctc tagacccatc aacccagtct ttgacatctt    2700
gttcttcaat agctccaaac ggagtctctc tgtatccaga gtatctaatc aattggttga    2760
ctctaatgga aatctttgac actatatgag tgctaacccc attagcaata cattgatcac    2820
aaattgtgtc tatggtctct gacagttgtg ttggagtttt acacttaacg ttgtgtagag    2880
cagcagacac aaacttggtg agtaaaggag tctcttcacc catgacaaaa aatcttgact    2940
taaactcagc aacaaaagtt cctatcacac tcttgggct gataaacttg tttaatttag    3000
aagataagaa ttcatggaag cacaccattt ccagcagttc tgtcctgtct tgaaactttt    3060
catcactaag gcaaggaatt tttataaggc taacctggtc atcgctggag gtataagtga    3120
caggtatcac atcatacaat aagtcaagtg cataacacag aaattgttca gtaattagcc    3180
catataaatc tgatgtgttg tgcaagattc cctggcccat gtccaagaca gacattatat    3240
ggctggggac ctggtccctt gactgcagat actggtgaaa aaactcttca ccaacactag    3300
tacagtcaca acccattaaa cctaaagatc tcttcaattt ccctacacag taggcttctg    3360
caacattaat tggaacttca acgaccttat gaagatgcca tttgagaatg ttcattactg    3420
gttcaagatt cacctttgtt ctatctctgg gattcttcaa ttctaatgtg tacaaaaaag    3480
aaaggaaaag tgctgggctc atagttggtc cccatttgga gtggtcatat gaacaggaca    3540
agtcaccatt gttaacagcc attttcatat cacagattgc acgttcgaat tccttttctg    3600
aattcaagca tgtgtatttc attgaactac ccacagcttc tgagaagtct tcaactaacc    3660
tggtcatcag cttagtgttg aggtctccca catacagttc tctatttgag ccaacctgct    3720
ccttataact tagtccaaat ttcaagttcc ctgtatttga gctgatgctt gtgaactctg    3780
taggagagtc gtctgaatag aaacataaat tccgtagggc tgcatttgta aaataacttt    3840
tgtctagctt atcagcaatg gcttcagaat tgctttccct ggtactaagc cgaacctcat    3900
cctttagtct cagaacttca ctggaaaagc ccaatctaga tctacttcta tgctcataac    3960
tacccaattt ctgatcataa tgtccttgaa ttaaaagata cttgaagcat tcaaagaatt    4020
```

```
catcttcttg gtaggctatt gttgtcaaat ttttaataa caaacccaaa gggcagatgt   4080
cctgcggtgc ttcaagaaaa taagtcaatt taaatggaga tagataaaca gcatcacata   4140
actctttata cacatcagac ctgagcacat ctggatcaaa atccttcacc tcatgcattg   4200
acacctctgc tttaatctct ctcaacactc aaaaggggc ccacaatgac tcaagagact   4260
ctcgctcatc aacagatgga tttttgatt tcaacttggt gatctcaact tttgtcccct   4320
cactattagc catcttggct agtgtcattt gtacgtcatt tctaataccc tcaaaggccc   4380
ttacttgatc ctctgttaaa ctctcataca tcactgataa ttcttcttga ttggttctgg   4440
ttcttgaacc ggtgctcaca agacctgtta gattttttaa tattaagtag tccatggaat   4500
caggatcaag attatacctg cctttgttt taaacctctc agccatagta gaaacgcatg   4560
ttgaaacaag tttctcctta tcataaacag aaagaatatt tccaagttcg tcgagcttgg   4620
ggattaccac acttttattg cttgacagat ccagagctgt gctagtgatg ttaggcctgt   4680
agggattgct tttcagttca cctgtaactt taagtcttcc tctattgaag agagaaatgc   4740
agaaggacaa aatctcttta cacactcctg gaatttgagt atctgaggaa gtcttagcct   4800
ctttggaaaa gaatctgtcc aatcctctta tcatggtgtc ctcttgttcc agtgttagac   4860
tcccacttag agggggggttt acaacaacac aatcaaactt gactttgggc tcaataaact   4920
tctcaaaaca cttgatttga tctgtcaggc gatcaggtgt ctctttggtt accaagtgac   4980
acagataact aacatttaat agatatttaa accttcttgc aaagtaaaga tctgcatctt   5040
cccctccacc caaaattgtc tggaaaagtt ccacagccat cctctgaatc agcacctctg   5100
atccagacat gcagtcgacc cttaactttg acatcaaatc cacatgatgg atttgatttg   5160
catatgccat caagaaatat cttagacctt gtaaaaatgt ctggttcctt ttggaagggg   5220
aacagagtac agctaacact aacaatctta atattggcct tgtcattgtc atgagttcgt   5280
ggctaaaatc caaccagctg gtcatttcct cacacatttc aattaacaca tcctccgaaa   5340 ataggcag gaaaaatctc tttggatcac agtaaaaaga gccttgttct tccaataccc   5400
cattgatgga tagatagata gaatagcacc ttgacttctc acctgttttt tggtaaaaca   5460
agagaccaaa tgtattcttt gtcagatgaa atctttgtac ataacactct cttagtctaa   5520
cattcccaaa atatctagaa tactctcttt cattgattaa caatcgggag gaaaatgatg   5580
tcttcatcga gttgaccaat gcaagggaaa tggaggacaa atcctaaat aatttcttct   5640 gctcaccttc cactaagctg ctgaatggct gatgtctaca gattttctca aattccttgt   5700
taatagtata tctcatcact ggtctgtcag aaacaagtgc ctgagctaaa atcatcaagc   5760
tatccatatc agggtgtttt attagttttt ccagctgtga ccagagatct tgatgagagt   5820
tcttcaatgt tctggaacac gcttgaaccc acttggggct ggtcatcaat ttcttcctta   5880
ttagtttaat cgcctccaga atatctagaa gtctgtcatt gactaacatt aacatttgtc   5940
caacaactat tcccgcattt cttaacctta caattgcatc atcatgcgtt ttgaaaagat   6000
cacaaagtaa attgagtaaa actaagtcca gaaacagtaa agtgtttctc ctggtgttga   6060 aaactttag acctttcact ttgttacaca cggaaagggc ttgaagataa cacctctcta   6120
cagcatcaat agatatagaa ttctcatctg actggctttc catgttgact tcatctattg   6180
gatgcaatgc gatagagtag actacatcca tcaacttgtt tgcacaaaaa gggcagctgg   6240
gcacatcact gtctttgtgg cttcctaata agatcaagtc atttataagc ttagactttt   6300
gtgaaaattt gaatttcccc aactgcttgt caaaaatctc cttcttaaac caaaacctta   6360
```

| | |
|---|---|
| actttatgag ttcttctctt atgacagatt ctctaatgtc tcctctaacc ccaacaaaga | 6420 |
| gggattcatt taacctctca tcataaccca aagaattctt tttcaagcat tcgatgtttt | 6480 |
| ctaatcccaa gctctggttt tttgtgttgg acaaactatg gatcaatcgc tggtattctt | 6540 |
| gttcttcaat attaatctct tgcataaatt ttgatttctt taggatgtcg atcagcaacc | 6600 |
| accgaactct ttcaacaacc caatcagcaa ggaatctatt gctgtagcta gatctgccat | 6660 |
| caaccacagg aaccaacgta atccctgccc ttagtaggtc ggactttagg tttaagagct | 6720 |
| ttgacatgtc actcttccat tttctctcaa actcatcagg attgaccta caaaggtttt | 6780 |
| ccaataggat gagtgttttc cctgtgagtt tgaagccatc cggaatgact tttggaaggg | 6840 |
| tgggacatag tatgccatag tcagacagga tcacatcaac aaacttctga tctgaattga | 6900 |
| tctgacaggc gtgtgcctca caggactcaa gctctactaa acttgacaga gtttgaacc | 6960 |
| cttccaacaa cagagagctg gggtgatgtt gagataaaaa gatgtccctt tggtatgcta | 7020 |
| gctcctgtct ttctggaaaa tgcttttctaa taaggctttt tatttcattt actgattcct | 7080 |
| ccatgctcaa gtgccgccta ggatccactg tgcg | 7114 |

<210> SEQ ID NO 5
<211> LENGTH: 3377
<212> TYPE: RNA
<213> ORGANISM: Lymphocytic choriomeningitis mammarenavirus Viruses (LCMV)
<220> FEATURE:
<223> OTHER INFORMATION: Lymphocytic choriomeningitis virus clone 13 segment S, complete sequence.ACCESSION DQ361065-VERSION D Q361065.2-GI:116563461.-ssRNA viruses; ssRNA negative-strand viruses; Arenaviridae; Mammarenavirus.

<400> SEQUENCE: 5

| | |
|---|---|
| gcgcaccggg gatcctaggc ttttggatt gcgctttcct ctagatcaac tgggtgtcag | 60 |
| gccctatcct acagaaggat gggtcagatt gtgacaatgt ttgaggctct gcctcacatc | 120 |
| atcgatgagg tgatcaacat tgtcattatt gtgcttatcg tgatcacggg tatcaaggct | 180 |
| gtctacaatt ttgccacctg tgggatattc gcattgatca gtttcctact tctggctggc | 240 |
| aggtcctgtg gcatgtacgg tcttaaggga cccgacattt acaaaggagt ttaccaattt | 300 |
| aagtcagtgg agtttgatat gtcacatctg aacctgacca tgcccaacgc atgttcagcc | 360 |
| aacaactccc accattacat cagtatgggg acttctggac tagaattgac cttcaccaat | 420 |
| gattccatca tcagtcacaa cttttgcaat ctgacctctg ccttcaacaa aaagaccttt | 480 |
| gaccacacac tcatgagtat agtttcgagc ctacacctca gtatcagagg gaactccaac | 540 |
| tataaggcag tatcctgcga cttcaacaat ggcataacca tccaatacaa cttgacattc | 600 |
| tcagatgcac aaagtgctca gagccagtgt agaaccttca gaggtagagt cctagatatg | 660 |
| tttagaactg ccttcggggg gaaatacatg aggagtggct ggggctggac aggctcagat | 720 |
| ggcaagacca cctggtgtag ccagacgagt taccaatacc tgattataca aaatagaacc | 780 |
| tgggaaaacc actgcacata tgcaggtcct tttgggatgt ccaggattct cctttcccaa | 840 |
| gagaagacta agttcctcac taggagacta gcgggcacat tcacctggac tttgtcagac | 900 |
| tcttcagggg tggagaatcc agtggttat tgcctgacca atggatgat tcttgctgca | 960 |
| gagcttaagt gtttcgggaa cacagcagtt gcgaaatgca atgtaaatca tgatgaagaa | 1020 |
| ttctgtgaca tgctgcgact aattgactac aacaaggctg ctttgagtaa gttcaaagag | 1080 |
| gacgtagaat ctgccttgca cttattcaaa acaacagtga attctttgat tcagatcaa | 1140 |
| ctactgatga ggaaccactt gagagatctg atgggggtgc catattgcaa ttactcaaag | 1200 |

```
ttttggtacc tagaacatgc aaagaccggc gaaactagtg tccccaagtg ctggcttgtc    1260
accaatggtt cttacttaaa tgagacccac ttcagtgacc aaatcgaaca ggaagccgat    1320
aacatgatta cagagatgtt gaggaaggat tacataaaga ggcaggggag taccccccta    1380
gcattgatgg accttctgat gttttccaca tctgcatatc tagtcagcat cttcctgcac    1440
cttgtcaaaa taccaacaca caggcacata aaaggtggct catgtccaaa gccacaccga    1500
ttaaccaaca aaggaatttg tagttgtggt gcatttaagg tgcctggtgt aaaaaccgtc    1560
tggaaaagac gctgaagaac agcgcctccc tgactctcca cctcgaaaga ggtggagagt    1620
cagggaggcc cagagggtct tagagtgtca caacatttgg gcctctaaaa attaggtcat    1680
gtggcagaat gttgtgaaca gttttcagat ctgggagcct tgctttggag gcgctttcaa    1740
aaatgatgca gtccatgagt gcacagtgcg gggtgatctc tttcttcttt ttgtcccctta   1800
ctattccagt atgcatctta cacaaccagc catatttgtc ccacactttg tcttcatact    1860
ccctcgaagc ttccctggtc atttcaacat cgataagctt aatgtccttc ctattctgtg    1920
agtccagaag ctttctgatg tcatcggagc cttgacagct tagaaccatc ccctgcggaa    1980
gagcacctat aactgacgag gtcaacccgg gttgcgcatt gaagaggtcg caagatcca     2040
tgccgtgtga gtacttggaa tcttgcttga attgtttttg atcaacgggt tccctgtaaa    2100
agtgtatgaa ctgcccgttc tgtggttgga aaattgctat ttccactgga tcattaaatc    2160
taccctcaat gtcaatccat gtaggagcgt tggggtcaat tcctcccatg aggtctttta    2220
aaagcattgt ctggctgtag cttaagccca cctgaggtgg acctgctgct ccaggcgctg    2280
gcctgggtga attgactgca ggtttctcgc ttgtgagatc aattgttgtg ttttcccatg    2340
ctctccccac aatcgatgtt ctacaagcta tgtatggcca tccttcacct gaaaggcaaa    2400
ctttatagag gatgttttca taagggttcc tgtccccaac ttggtctgaa acaaacatgt    2460
tgagttttct cttggccccg agaactgcct tcaagaggtc ctcgctgttg cttggcttga    2520
tcaaaattga ctctaacatg ttaccccat ccaacagggc tgccctgcc ttcacggcag       2580
caccaagact aaagttatag ccagaaatgt tgatgctgga ctgctgttca gtgatgaccc    2640
ccagaactgg gtgcttgtct ttcagccttt caagatcatt aagatttgga tacttgactg    2700
tgtaaagcaa gccaaggtct gtgagcgctt gtacaacgtc attgagcgga gtctgtgact    2760
gtttggccca caagccata gttagacttg gcattgtgcc aaattgattg ttcaaaagtg     2820
atgagtcttt cacatcccaa actcttacca caccacttgc accctgctga ggctttctca    2880
tcccaactat ctgtaggatc tgagatcttt ggtctagttg ctgtgttgtt aagttcccca    2940
tatataccc tgaagcctgg ggcctttcag acctcatgat cttggccttc agcttctcaa     3000
ggtcagccgc aagagacatc agttcttctg cactgagcct ccccactttc aaaacattct    3060
tctttgatgt tgactttaaa tccacaagag aatgtacagt ctggttgaga cttctgagtc    3120
tctgtaggtc tttgtcatct ctcttttcct tcctcatgat cctctgaaca ttgctgacct    3180
cagagaagtc caacccattc agaaggttgg ttgcatcctt aatgacagca gccttcacat    3240
ctgatgtgaa gctctgcaat tctcttctca atgcttgcgt ccattggaag ctcttaactt    3300
ccttagacaa ggacatcttg ttgctcaatg gtttctcaag acaaatgcgc aatcaaatgc    3360
ctaggatcca ctgtgcg                                                   3377
```

<210> SEQ ID NO 6
<211> LENGTH: 7229
<212> TYPE: RNA

<213> ORGANISM: Lymphocytic choriomeningitis mammarenavirus Viruses (LCMV)
<220> FEATURE:
<223> OTHER INFORMATION: Lymphocytic choriomeningitis virus clone 13 segment L, complete sequence.-ACCESSION DQ361066-VERSION DQ361066.1-GI:86440167.-ssRNA viruses; ssRNA negative-strand viruses; Arenaviridae; Mammarenavirus

<400> SEQUENCE: 6

| | | | | | |
|---|---|---|---|---|---|
| gcgcaccggg | gatcctaggc | gtttagttgc | gctgtttggt | tgcacaactt | tcttcgtgag | 60 |
| gctgtcagaa | gtggacctgg | ctgatagcga | tgggtcaagg | caagtccaga | gaggagaaag | 120 |
| gcaccaatag | tacaaacagg | gccgaaatcc | taccagatac | cacctatctt | ggcccttaa | 180 |
| gctgcaaatc | ttgctggcag | aaatttgaca | gcttggtaag | atgccatgac | cactaccttt | 240 |
| gcaggcactg | tttaaacctt | ctgctgtcag | tatccgacag | gtgtcctctt | tgtaaatatc | 300 |
| cattaccaac | cagattgaag | atatcaacag | ccccaagctc | tccacctccc | tacgaagagt | 360 |
| aacaccgtcc | ggccccggcc | ccgacaaaca | gcccagcaca | agggaaccgc | acgtcaccca | 420 |
| acgcacacag | acacagcacc | caacacagaa | cacgcacaca | cacacacaca | cacccaca | 480 |
| cgcacgcgcc | cccaccaccg | gggggcgccc | cccccgggg | ggcggccccc | cgggagcccg | 540 |
| ggcggagccc | cacggagatg | cccatcagtc | gatgtcctcg | gccaccgacc | cgcccagcca | 600 |
| atcgtcgcag | gacctcccct | tgagtctaaa | cctgccccc | actgtttcat | acatcaaagt | 660 |
| gctcctagat | ttgctaaaac | aaagtctgca | atccttaaag | gcgaaccagt | ctggcaaaag | 720 |
| cgacagtgga | atcagcagaa | tagatctgtc | tatacatagt | tcctggagga | ttacacttat | 780 |
| ctctgaaccc | aacaaatgtt | caccagttct | gaatcgatgc | aggaagaggt | tcccaaggac | 840 |
| atcactaatc | ttttcatagc | cctcaagtcc | tgctagaaag | actttcatgt | ccttggtctc | 900 |
| cagcttcaca | atgatatttt | ggacaaggtt | tcttccttca | aaaagggcac | ccatcttac | 960 |
| agtcagtggc | acaggctccc | actcaggtcc | aactctctca | aagtcaatag | atctaatccc | 1020 |
| atccagtatt | cttttggagc | ccaacaactc | aagctcaaga | gaatcaccaa | gtatcaaggg | 1080 |
| atcttccatg | taatcctcaa | actcttcaga | tctgatatca | aagacaccat | cgttcacctt | 1140 |
| gaagacagag | tctgtcctca | gtaagtggag | gcattcatcc | aacattcttc | tatctatctc | 1200 |
| acccttaaag | aggtgagagc | atgataaaag | ttcagccaca | cctggattct | gtaattggca | 1260 |
| cctaaccaag | aatatcaatg | aaaatttcct | taaacagtca | gtattattct | gattgtgcgt | 1320 |
| aaagtccact | gaaattgaaa | actccaatac | cccttttgtg | tagttgagca | tgtagtccca | 1380 |
| cagatccttt | aaggatttaa | atgcctttgg | gtttgtcagg | ccctgcctaa | tcaacatggc | 1440 |
| agcattacac | acaacatctc | ccattcggta | agagaaccac | ccaaaaccaa | actgcaaatc | 1500 |
| attcctaaac | ataggcctct | ccacattttt | gttcaccacc | tttgagacaa | atgattgaaa | 1560 |
| ggggcccagt | gcctcagcac | catcttcaga | tggcatcatt | tctttatgag | ggaaccatga | 1620 |
| aaaattgcct | aatgtcctgg | ttgttgcaac | aaattctcga | acaaatgatt | caaaatacac | 1680 |
| ctgttttaag | aagttcttgc | agacatccct | cgtgctaaca | acaaattcat | caaccagact | 1740 |
| ggagtcagat | cgctgatgag | aattggcaag | gtcagaaaac | agaacagtgt | aatgttcatc | 1800 |
| ccttttccac | ttaacaacat | gagaaatgag | tgacaaggat | tctgagttaa | tatcaattaa | 1860 |
| aacacagagg | tcaaggaatt | taattctggg | actccacctc | atgttttttg | agctcatgtc | 1920 |
| agacataaat | ggaagaagct | gatcctcaaa | gatcttggga | tatagccgcc | tcacagattg | 1980 |
| aatcacttgg | ttcaaattca | ctttgtcctc | cagtagcctt | gagctctcag | gctttcttgc | 2040 |
| tacataatca | catgggttta | agtgcttaag | agttaggttc | tcactgttat | tcttcccttt | 2100 |

```
ggtcggttct gctaggaccc aaacacccaa ctcaaaagag ttgctcaatg aaatacaaat      2160
gtagtcccaa agaagaggcc ttaaaaggca tatatgatca cggtgggctt ctggatgaga      2220
ctgtttgtca caaatgtaca gcgttatacc atcccgattg caaactcttg tcacatgatc      2280
atctgtggtt agatcctcaa gcagcttttt gatatacaga ttttccctat ttttgtttct      2340
cacacacctg cttcctagag ttttgcaaag gcctataaag ccagatgaga tacaactctg      2400
gaaagctgac ttgttgattg cttctgacag cagcttctgt gcacccctttg tgaatttact     2460 acaaagtttg ttctggagtg tcttgatcaa tgatgggatt ctttcctctt ggaaagtcat      2520
cactgatgga taaccacct tttgtcttaa aaccatcctt aatgggaaca tttcattcaa       2580
attcaaccag ttaacatctg ctaactgatt cagatcttct tcaagaccga ggaggtctcc      2640
caattgaaga atggcctcct ttttatctct gttaaatagg tctaagaaaa attcttcatt      2700
aaattcacca tttttgagct tatgatgcag tttccttaca agctttctta caacctttgt      2760
ttcattagga cacagttcct caatgagtct ttgtattctg taacctctag aaccatccag      2820
ccaatctttc acatcagtgt tggtattcag tagaaatgga tccaaaggga aattggcata      2880
ctttaggagg tccagtgttc tcctttggat actattaact agggagactg ggacgccatt      2940
tgcgatggct tgatctgcaa ttgtatctat tgtttcacaa agttgatgtg gctctttaca      3000
cttgacattg tgtagcgctg cagatacaaa ctttgtgaga gagggactt cctcccccca       3060 tacatagaat ctagatttaa attctgcagc gaacctccca gccacacttt tgggctgat       3120 aaatttgttt aacaagccgc tcagatgaga ttggaattcc aacaggacaa ggacttcctc      3180
cggatcactt acaaccaggt cactcagcct cctatcaaat aaagtgatct gatcatcact      3240
tgatgtgtaa gcctctggtc tttcgccaaa gataacacca atgcagtagt tgatgaacct      3300
ctcgctaagc aaaccataga agtcagaagc attatgcaag attccctgcc ccatatcaat      3360
aaggctggat atatgggatg gcactatccc cattttcaaaa tattgtctga aaattctctc     3420
agtaacagtt gtttctgaac ccctgagaag ttttagcttc gacttgacat atgatttcat      3480
cattgcattc acaacaggaa aggggacctc gacaagctta tgcatgtgcc aagttaacaa      3540
agtgctaaca tgatctttcc cggaacgcac atactggtca tcacctagtt tgagattttg      3600
tagaaacatt aagaacaaaa atgggcacat cattggtccc catttgctgt gatccatact      3660
atagtttaag aaccccttccc gcacattgat agtcattgac aagattgcat ttcaaattc      3720 cttatcattg tttaaacagg agcctgaaaa gaaacttgaa aaagactcaa ataatcttc       3780 tattaacctt gtgaacattt ttgtcctcaa atctccaata tagagttctc tatttccccc      3840
aacctgctct ttataagata gtgcaaattt cagccttcca gagtcaggac ctactgaggt      3900
gtatgatgtt ggtgattctt ctgagtagaa gcacagattt tcaaagcag cactcataca       3960 ttgtgtcaac gacagagctt tactaaggga ctcagaatta cttttccctct cactgattct      4020 cacgtcttct tccagtttgt cccagtcaaa tttgaaattc aagccttgcc tttgcatatg      4080
cctgtatttc cctgagtacg catttgcatt catttgcaac agaatcatct tcatgcaaga      4140
aaaccaatca ttctcagaaa agaactttct acaaaggttt tttgccatct catcgaggcc      4200
acactgatct ttaatgactg aggtgaaata caaaggtgac agctctgtgg aaccctcaac      4260
agcctcacag ataaatttca tgtcatcatt ggttagacat gatgggtcaa agtcttctac      4320
taaatggaaa gatatttctg acaagataac ttttcttaag tgagccatct tccctgttag      4380
aataagctgt aaatgatgta gtccttttgt atttgtaagt ttttctccat ctcctttgtc      4440
```

-continued

| | | | | | |
|---|---|---|---|---|---|
| attggccctc | ctacctcttc | tgtaccgtgc | tattgtggtg | ttgaccttt | cttcgagact | 4500 |
| tttgaagaag | cttgtctctt | cttctccatc | aaaacatatt | tctgccaggt | tgtcttccga | 4560 |
| tctccctgtc | tcttctccct | tggaaccgat | gaccaatcta | gagactaact | tggaaacttt | 4620 |
| atattcatag | tctgagtggc | tcaacttata | cttttgtttt | cttacgaaac | tctccgtaat | 4680 |
| ttgactcaca | gcactaacaa | gcaatttgtt | aaagtcatat | tccagaagtc | gttctccatt | 4740 |
| tagatgctta | ttaaccacca | cacttttgtt | actagcaaga | tctaatgctg | tcgcacatcc | 4800 |
| agagttagtc | atgggatcta | ggctgtttag | cttcttctct | cctttgaaaa | ttaaagtgcc | 4860 |
| gttgttaaat | gaagacacca | ttaggctaaa | ggcttccaga | ttaacacctg | gagttgtatg | 4920 |
| ctgacagtca | atttctttac | tagtgaatct | cttcatttgc | tcatagaaca | cacattcttc | 4980 |
| ctcaggagtg | attgcttcct | tggggttgac | aaaaaaacca | aattgacttt | tgggctcaaa | 5040 |
| gaacttttca | aaacatttta | tctgatctgt | tagcctgtca | ggggtctcct | ttgtgatcaa | 5100 |
| atgcacagg | tatgacacat | tcaacataaa | ttttaaatttt | gcactcaaca | acaccttctc | 5160 |
| accagtacca | aaaatagttt | ttattaggaa | tctaagcagc | ttatacacca | ccttctcagc | 5220 |
| aggtgtgatc | agatcctccc | tcaacttatc | cattaatgat | gtagatgaaa | aatctgacac | 5280 |
| tattgccatc | accaaatatc | tgacactctg | tacctgcttt | tgatttctct | ttgttgggtt | 5340 |
| ggtgagcatt | agcaacaata | gggtcctcag | tgcaacctca | atgtcggtga | gacagtcttt | 5400 |
| caaatcagga | catgatctaa | tccatgaaat | catgatgtct | atcatattgt | ataagacctc | 5460 |
| atctgaaaaa | attggtaaaa | agaaccttt | aggatctgca | tagaaggaaa | ttaaatgacc | 5520 |
| atccgggcct | tgtatggagt | agcaccttga | agattctcca | gtcttctggt | ataataggtg | 5580 |
| gtattcttca | gagtccagtt | ttattacttg | gcaaaacact | tctttgcatt | ctaccacttg | 5640 |
| atatctcaca | gaccctattt | gattttgcct | tagtctagca | actgagctag | ttttcatact | 5700 |
| gtttgttaag | gccagacaaa | cagatgataa | tcttctcagg | ctctgtatgt | tcttcagctg | 5760 |
| ctctgtgctg | ggtggaaat | tgtaatcttc | aaacttcgta | taatacatta | tcgggtgagc | 5820 |
| tccaattttc | ataaagttct | caaattcagt | gaatggtatg | tggcattctt | gctcaaggtg | 5880 |
| ttcagacagt | ccgtaatgct | cgaaactcag | tcccaccact | aacaggcatt | tttgaatttt | 5940 |
| tgcaatgaac | tcactaatag | atgccctaaa | caattcctca | aaagacacct | ttctaaacac | 6000 |
| ctttgacttt | tttctattcc | tcaaaagtct | aatgaactcc | tctttagtgc | tgtgaaagct | 6060 |
| taccagccta | tcattcacac | tactatagca | acaacccacc | cagtgtttat | cattttttaa | 6120 |
| cccttgaat | ttcgactgtt | ttatcaatga | ggaaagacac | aaaacatcca | gatttaacaa | 6180 |
| ctgtctcctt | ctagtattca | acagtttcaa | actcttgact | ttgtttaaca | tagagaggag | 6240 |
| cctctcatat | tcagtgctag | tctcacttcc | cctttcgtgc | ccatgggtct | ctgcagttat | 6300 |
| gaatctcatc | aaaggacagg | attcgactgc | ctccctgctt | aatgttaaga | tatcatcact | 6360 |
| atcagcaagg | ttttcataga | gctcagagaa | ttccttgatc | aagccttcag | ggtttacttt | 6420 |
| ctgaaagttt | ctctttaatt | tcccactttc | taaatctctt | ctaaacctgc | tgaaaagaga | 6480 |
| gtttattcca | aaaaccacat | catcacagct | catgttgggg | ttgatgccctt | cgtggcacat | 6540 |
| cctcataatt | tcatcattgt | gagttgacct | cgcatcttc | agaattttca | tagagtccat | 6600 |
| accggagcgc | ttgtcgatag | tagtcttcag | ggactcacag | agtctaaaat | attcagactc | 6660 |
| ttcaaagact | ttctcatttt | ggttagaata | ctccaaaagt | ttgaataaaa | ggtctctaaa | 6720 |
| tttgaagttt | gcccactctg | gcataaaact | attatcataa | tcacaacgac | catctactat | 6780 |
| tggaactaat | gtgacacccg | caacagcaag | gtcttccctg | atgcatgcca | atttgttagt | 6840 |

-continued

```
gtcctctata aatttcttct caaaactggc tggagtgctc ctaacaaaac actcaagaag   6900
aatgagagaa ttgtctatca gcttgtaacc atcaggaatg ataagtggta gtcctgggca   6960
tacaattcca gactccacca aaattgtttc cacagactta tcgtcgtggt tgtgtgtgca   7020
gccactcttg tctgcactgt ctatttcaat gcagcgtgac agcaacttga gtccctcaat   7080
cagaaccatt ctgggttccc tttgtcccag aaagttgagt ttctgccttg acaacctctc   7140
atcctgttct atatagttta aacataactc tctcaattct gagatgattt catccattgc   7200
gcatcaaaaa gcctaggatc ctcggtgcg                                      7229
```

METHOD OF ENHANCING INNATE IMMUNE RESPONSES AGAINST A TUMOR COMPRISING ADMINISTERING LYMPHOCYTIC CHORIOMENINGITIS VIRUS (LCMV)

CROSS-REFERENCE TO RELATED APPLICATIONS

The present application is divisional application of U.S. patent application Ser. No. 15/567,343, filed Oct. 17, 2017, which is the United States National stage patent application of International Application No. PCT/EP2016/058347, filed Apr. 15, 2016, which claims the right of priority of German patent application No. 102015207036.0 filed Apr. 17, 2015, with the German Patent Office, the entire contents of each of which are incorporated herein for all purposes.

SEQUENCE LISTING

The instant application contains a Sequence Listing which has been submitted in ASCII format via EFS-Web and is hereby incorporated by reference in its entirety. Said ASCII copy, created on Feb. 1, 2019, is named SCH-5000-DV_SeqListing.txt and is 43 kilobytes in size.

FIELD OF THE INVENTION

The invention relates to arenaviruses for use in the treatment and/or prevention of tumors and also methods for preparing arenaviruses with (improved) tumor-regressive properties.

Arenaviruses belong to the family of human pathogenic, pleomorphic RNA viruses. Diseases with these viruses belong to the zoonoses due to their natural reservoir in animals, predominantly rodents. Zoonoses refer to diseases that can be transferred from the animal to humans and vice versa from humans to the animal.

At least eight arenaviruses are known to cause illness in humans. Typical are aseptic meningitis and haemorrhagic fever. Known viruses which can trigger a disease in humans are the lymphocytic choriomeningitis virus (LCMV), Guanarito virus (GTOV), Junin virus (JUNV), Lassa virus (LASV), Lujo virus (LUJV) Machupo virus (MACV), Sabia virus (SABV) and the Whitewater Arroyo virus (WWAV).

Arenaviruses are generally divided into two groups, namely the Old World arenaviruses and the New World arenaviruses. These groups differ geographically and genetically. Old World arenaviruses, such as the lymphocytic choriomeningitis virus, have been found in countries of the eastern hemisphere, such as European, Asian and African countries. In contrast, New World arenaviruses have been found in countries of the western hemisphere, such as Argentina, Bolivia, Venezuela, Brazil and the United States of America.

The name of the virus family is derived from the Latin arenosus (sandy) and arena (sand) to describe the sandy ribosomal structure within the virions. The virions of the arenaviruses have a round to irregular shape and have a diameter, depending on species and preparation of the test material, from 50 nm to 300 nm, usually between 110 nm and 130 nm. Club-shaped glycoprotein spikes, 8 nm to 10 nm long, are embedded in the virus envelope. The individual spikes consist of a tetramer of the viral envelope protein.

The virions also comprise two closed-ring capsids with helical symmetry. The length of the capsids varies between 450 nm and 1300 nm. One molecule of the viral RNA (ribonucleic acid) polymerase (L-protein) is attached to each of them.

Each capsid comprises one molecule of a single-stranded RNA with mixed (i.e. ambisense, +/−) polarity. The two single-stranded RNA molecules represent the viral genome. They are referred to as L (large) and S (small) and are about 7.5 kb (kilobases) or 3.5 kb (kilobases) large. Although the capsids are closed ring-shaped, the RNA strands are linear and thus not circular. A 19 to 30 base long sequence at the 3' end of the RNA is present on both strands and is also conserved within the virus family.

Very exceptional morphologically is the presence of an alternating number of cellular ribosomes within the virions, which give the viral particles their "sandy" appearance. Similarly, in purified virus preparations, a number of different cellular RNAs (also including ribosomal RNA) and also replicative forms of viral RNA are found, as are diverse viral mRNAs (messenger ribonucleic acids bound to the ribosomes) and complete complementary strands of the virus genome. These non-genomic RNAs are found in varying amounts all lying outside the abovementioned capsids.

The use of arenaviruses as vaccination vectors is known. A prominent example is the vaccination virus Candid #1 used against Argentinian hemorrhagic fever. This is a vaccination variant of the Junin virus.

Known from WO 2009/083210 A1 is the use of replication defects, i.e. genetically modified arenavirus particles (virions), inter alia, for the treatment of neoplastic diseases such as, for example, melanoma, prostate carcinoma, breast carcinoma and lung carcinoma. In the publication "Development of replication-defective lymphocytic choriomeningitis virus vectors for the induction of potent $CD8^+$ T cell immunity" (Nature Medicine, Vol. 16, No. 3, March 2010, pp. 339-345; doi: 10.1038/Nm.2104), cancer immunotherapy is mentioned as a potential area of application for such viral particles.

Furthermore, WO 2006/008074 A1 discloses the use of packaging cells, which produce retroviral virions pseudotyped with arenavirus glycoprotein, for gene therapy of solid tumors.

The methods for the treatment of tumors described in the prior art are based on the use of virus particles which are very complicated to produce by genetic engineering. In the case of gene therapy treatment methods, it is frequently not possible to achieve adequate, therapeutically effective transduction of the tumor tissue with genetically engineered virions or packaging cells which produce virions.

SUMMARY OF THE INVENTION

Object and Solution

The present invention is therefore based on the object of providing a simpler and, in particular, more efficient therapeutic solution for tumors, in particular carcinomas and sarcomas, compared to the prior art.

This object is achieved according to the invention by an arenavirus according to independent claim 1, by a medicament according to claim 14 and also by an in vitro method according to independent claim 15. Preferred embodiments are defined in the dependent claims. The wording of all claims is hereby incorporated by reference into the content of the description. An additional subject of the invention, which achieves the object of the invention, is disclosed in the description.

According to a first aspect, the invention relates to an arenavirus for use in the treatment and/or prevention of a tumor, preferably a malignant tumor, in humans or animals.

The arenavirus is preferably characterized in that it is free of genomic foreign RNA, i.e. it does not comprise any genomic foreign RNA. In other words, the genome of the arenavirus is preferably free of foreign RNA or preferably comprises no foreign RNA.

In the context of the present invention, the expression "genomic foreign RNA" is intended to mean an RNA (ribonucleic acid) or RNA sequence which does not occur or is not present in the genome of a wild-type arenavirus or in the genome of a mutant of a wild-type arenavirus (mutated arenavirus), in particular in the genome of a natural mutant of a wild-type arenavirus (naturally mutated arenavirus). Examples of foreign RNA are artificial or synthetic RNA molecules, RNA of organisms and RNA from other viruses.

In the context of the present invention, (in accordance with the understanding of those skilled in the art), the expression "wild-type arenavirus" is understood to mean an arenavirus whose genome is the genetically normal form occurring in nature.

In the context of the present invention, (in accordance with the understanding of those skilled in the art), the expression "mutant of a wild-type arenavirus" or "mutated arenavirus" is understood to mean an arenavirus whose genome comprises a spontaneous, i.e. naturally-induced, modification or modification induced by mutagenesis, compared to the wild-type genome.

Accordingly, in the context of the present invention, (in accordance with the understanding of those skilled in the art), the expression "natural mutant of a wild-type arenavirus" or "naturally mutated arenavirus" is understood to mean an arenavirus whose genome comprises a spontaneous, i.e. naturally-induced, modification, compared to the wild-type genome. A naturally mutated arenavirus can be produced preferably by passage, in particular serial passage, which will be discussed in more detail below.

The invention is based on the surprising finding that arenaviruses without genomic foreign RNA are able to effect tumor regression. Tumor regression is due to an activation or stimulation of congenital and adaptive immune cells caused by the arenaviruses. The activated immune cells secrete increased antitumoral cytokines such as interferon-$\alpha$ and interferon-$\gamma$, thereby counteracting or repelling the tumor. A further surprising finding is the realization that the arenaviruses cause a significantly increased secretion of antitumoral cytokines in the case of a tumor manifestation. Arenaviruses without genomic foreign RNA are thus suitable for use in tumor treatment. This has been successfully verified by the applicant by means of animal experiments. For this purpose, mice were used, inter alia, in which growth of human tumors is possible.

In a further embodiment, the arenavirus is also free of non-genomic foreign RNA. In the context of the present invention, the expression "non-genomic foreign RNA" is intended to mean an RNA or RNA sequence, apart from the arenavirus genome, which does not occur or is not present in a wild-type arenavirus or a mutant of a wild-type arenavirus (mutated arenavirus), in particular of a natural mutant of a wild-type arenavirus (naturally mutated arenavirus). In other words, in this embodiment the arenavirus does not comprise overall any foreign RNA, i.e neither genomic foreign RNA nor non-genomic foreign RNA.

In a preferred embodiment, the arenavirus is a wild-type arenavirus.

In a further embodiment, the arenavirus is a natural mutant of a wild-type arenavirus, i.e. a naturally mutated arenavirus.

The natural mutant or the naturally mutated arenavirus is preferably produced by passage, in particular multiple passage, in host animals and/or host cells.

The natural mutant or the naturally mutated arenavirus is particularly preferably produced by serial passage in host animals and/or host cells.

The arenavirus provided according to the invention is thus preferably an arenavirus which is produced starting from its wild-type form by passage, preferably serial passage, in host animals and/or host cells.

The host animals mentioned in the preceding paragraphs are preferably rodents, particularly mice. The host cells mentioned in the previous paragraphs, on the other hand, are preferably dendritic cells or tumor cells.

In the context of the present invention, in accordance with the understanding of those skilled in the art, the term "passage" is understood to mean a multiple, regular introduction of the arenavirus into host animals and/or host cells. In the context of the present invention, in accordance with the understanding of those skilled in the art, the expression "serial passage" is understood to mean a multiple, regular introduction of the arenavirus into different host animals, preferably of the same type, and/or different cells, preferably of the same type. Due to the multiple changes of environment (host animal and/or host cell), the arenavirus is subject to an increased adaptation pressure or mutational pressure, thereby increasing the likelihood of advantageous mutations occurring in the genome of the arenavirus from the perspective of tumor regression.

In a further embodiment, the tumor is selected from the group comprising or consisting of carcinoma, melanoma, blastoma, lymphoma and sarcoma.

In the context of the present invention, (in accordance with the understanding of those skilled in the art), the term "carcinoma" is intended to mean malignant neoplasia of epithelial origin.

In the context of the present invention, (in accordance with the understanding of those skilled in the art), the term "sarcoma" is intended to mean malignant neoplasia of mesodermal origin.

In the context of the present invention, (in accordance with the understanding of those skilled in the art), the term "melanoma" is intended to mean malignant neoplasia of melanocytic origin.

In the context of the present invention, (in accordance with the understanding of those skilled in the art), the term "lymphoma" is intended to mean malignant neoplasia of lymphocytic origin.

In the context of the present invention, (in accordance with the understanding of those skilled in the art), the term "blastoma" is intended to mean malignant neoplasia of embryonic origin.

In a preferred embodiment, the carcinoma is selected from the group comprising or consisting of anal carcinoma, bronchial carcinoma, lung carcinoma, endometrial carcinoma, gallbladder carcinoma, hepatocellular carcinoma, testicular carcinoma, colorectal carcinoma, laryngeal carcinoma, oesophogeal cancer, gastric carcinoma, breast carcinoma, renal carcinoma, ovarian carcinoma, pancreas tumor, pharyngeal carcinoma, prostate carcinoma, thyroid carcinoma and cervical carcinoma.

In a preferred embodiment, the sarcoma is selected from the group comprising or consisting of angiosarcoma, chondrosarcoma, Ewing's sarcoma, fibrosarcoma, Kaposi's sarcoma, liposarcoma, leiomyosarcoma, malignant fibrous histiocytoma, neurogenic sarcoma, osteosarcoma and rhabdomyosarcoma.

In a preferred embodiment, the arenavirus is an Old World arenavirus which is preferably selected from the group comprising or consisting of Ippy virus (IP-PYV), Lassa virus (LASV), lymphocytic choriomeningitis virus (LCMV), Mobala virus (MOBV) and Mopeia virus (MOPV).

In a particularly preferred embodiment, the arenavirus is the lymphocytic choriomeningitis virus, preferably a strain which is selected from the group comprising or consisting of WE, Armstrong, Clone 13 and Docile.

In a preferred embodiment, the arenavirus is a New World arenavirus, which is preferably selected from the group comprising or consisting of Allpaahuayo virus (ALLV), Amapari virus (AMAV), Bear Canyon virus (BCNV), Chapare virus, Cupixi virus (CPXV), Flexal virus (FLEV), Guanarito virus (GTOV), Junin virus (JUNV), Latino virus (LATV), Machupo virus (MACV), Oliveros virus (OLVV), Parana virus (PARV), Pichinde virus (PICV), Pirital virus (PIRV), Sabia virus (SABV), Tacaribe virus (TCRV), Tamiami virus (TAMV) and Whitewara Arroyo virus (WWAV).

In a particularly preferred embodiment, the arenavirus is a Junin virus, in particular the strain Candid #1 (Candid No. 1).

In a further embodiment, the Junin virus, in particular the strain Candid #1 (Candid No. 1), has a nucleic acid sequence, in particular an S-ribonucleic acid sequence or ambisense sequence, according to SEQ ID No. 1 (according to sequence listing).

In a further embodiment, the Junin virus, in particular the strain Candid #1 (Candid No. 1), has a nucleic acid sequence, in particular an L-ribonucleic acid sequence or ambisense sequence, according to SEQ ID No. 2 (according to sequence listing).

In a further embodiment, the Junin virus, in particular the strain Candid #1 (Candid No. 1), has a nucleic acid sequence, in particular an S-ribonucleic acid sequence or ambisense sequence, according to SEQ ID No. 3 (according to sequence listing).

In a further embodiment, the Junin virus, in particular the strain Candid #1 (Candid No. 1), has a nucleic acid sequence, in particular an L-ribonucleic acid sequence or ambisense sequence, according to SEQ ID No. 4 (according to sequence listing).

In a further embodiment, the lymphocytic choriomeningitis virus (LCMV virus) mentioned above has a nucleic acid sequence, in particular an S-ribonucleic acid sequence or ambisense sequence, according to SEQ ID No. 5 (according to sequence listing).

In a further embodiment, the lymphocytic choriomeningitis virus (LCMV virus) mentioned above has a nucleic acid sequence, in particular an L-ribonucleic acid sequence or ambisense sequence, according to SEQ ID No. 6 (according to sequence listing).

In a further embodiment, the arenavirus is isolated from tumor lysates, organ lysates, urine or blood.

In an alternative embodiment, the arenavirus is isolated from a cell culture medium, in particular from a human tumor cell line.

In a further embodiment, the arenavirus is for administration in the form of virions, i.e. in the form of arenavirus particles, which are outside a cell.

In a further embodiment, the arenavirus is provided, preferably prepared, for local, in particular intramuscular, intraperitoneal or subcutaneous administration. In other words, the arenavirus is used in a further embodiment for local, in particular intramuscular, intraperitoneal or subcutaneous administration.

Preferably the arenavirus is provided, preferably prepared, for local administration at a dose of 1 PFU (Plaque Forming Unit)/kg body weight to $10^{12}$ PFU/kg body weight, particularly $10^2$ PFU/kg body weight to $10^6$ PFU/kg body weight, preferably $10^3$ PFU/kg body weight to $10^5$ PFU/kg body weight. In other words, the arenavirus is used, preferably for local administration, at a dose of 1 PFU (Plaque Forming Unit)/kg body weight to $10^{12}$ PFU/kg body weight, particularly $10^2$ PFU/kg body weight to $10^6$ PFU/kg body weight, preferably $10^3$ PFU/kg body weight to $10^5$ PFU/kg body weight.

In an alternative embodiment, the arenavirus is provided, preferably prepared, for systemic, in particular intravenous, administration. In other words, the arenavirus is used in an alternative embodiment for systemic, in particular intravenous, administration.

Preferably, the arenavirus is provided, preferably prepared, for systemic administration at a dose of 1 PFU/kg body weight to $10^{12}$ PFU/kg body weight, particularly $10^2$ PFU/kg body weight to $10^6$ PFU/kg body weight, preferably $10^3$ PFU/kg body weight to $10^5$ PFU/kg body weight. In other words, the arenavirus is used, preferably for systemic administration, at a dose of 1 PFU/kg body weight to $10^{12}$ PFU/kg body weight, particularly $10^2$ PFU/kg body weight to $10^6$ PFU/kg body weight, preferably $10^3$ PFU/kg body weight to $10^5$ PFU/kg body weight.

According to a second aspect, the invention relates to a medicament for use in the treatment and/or prevention of a tumor, in particular a malignant tumor.

The medicament is characterized in particular by the fact that it has an arenavirus according to the first aspect of the invention.

The medicament preferably further comprises a pharmaceutically acceptable carrier. The carrier may in particular be selected from the group comprising or consisting of water, saline solution, buffer solution and cell culture medium.

In a further embodiment, the medicament also comprises an active ingredient. The active ingredient can in particular be a cytostatic agent, an antibody and/or a cytokine.

With regard to further features and advantages of the medicament, in particular of the arenavirus and also the tumor, reference is made fully to the present description in order to avoid repetitions.

According to a third aspect, the invention relates to a method for producing an arenavirus with tumor-regressive, i.e. tumor-repelling/counteracting properties or improved tumor-regressive properties.

The tumor is preferably a malignant tumor, preferably a carcinoma, melanoma, blastoma, lymphoma or sarcoma. Accordingly, the method is preferably a method for producing an arenavirus with (improved) carcinoma-, melanoma-, blastoma-, lymphoma- or sarcoma-regressive properties.

The method comprises the following steps:

a) infecting dendritic cells or tumor cells with an arenavirus, b) culturing the arenavirus in the infected dendritic cells or infected tumor cells and c) isolating the cultured arenavirus or a subset of the cultured arenavirus from the infected dendritic cells or infected tumor cells.

The sequence of steps a) to c) may also be referred to as a (single) passage of the arenavirus in the dendritic cells or tumor cells.

In a preferred embodiment, the arenavirus is an arenavirus which has been subjected to a serial passage in host animals prior to carrying out step a). For further details and advantages, reference may be made to the corresponding statements made in the context of the fourth aspect of the invention.

In a further embodiment, the dendritic cells or tumor cells are in the form of a cell culture (dendritic cell culture or tumor cell culture).

The tumor cells are preferably malignant tumor cells, in particular carcinoma, melanoma, blastoma, lymphoma or sarcoma cells.

The carcinoma cells may be selected from the group comprising or consisting of anal carcinoma cells, bronchial carcinoma cells, lung carcinoma cells, endometrial carcinoma cells, gallbladder carcinoma cells, hepatocellular carcinoma cells, testicular carcinoma cells, colorectal carcinoma cells, laryngeal carcinoma cells, oesophogeal carcinoma cells, gastric carcinoma cells, breast carcinoma cells, renal carcinoma cells, ovarian carcinoma cells, pancreas tumor cells, pharyngeal carcinoma cells, prostate carcinoma cells, thyroid carcinoma cells and cervical carcinoma cells.

The sarcoma cells may be selected from the group comprising or consisting of angiosarcoma cells, chondrosarcoma cells, Ewing's sarcoma cells, fibrosarcoma cells, Kaposi's sarcoma cells, liposarcoma cells, leiomyosarcoma cells, malignant fibrous histiocytoma cells, neurogenic sarcoma cells, osteosarcoma cells and rhabdomyosarcoma cells.

In a further embodiment, the tumor cells are immortalized immune cells, in particular immortalized macrophages.

The dendritic cells or tumor cells are infected according to step a) preferably by adding the arenavirus to the cells.

In a preferred embodiment, the sequence of steps a) to c) is repeated with new, in particular non-infected, dendritic cells, preferably of the same type, or with new, in particular non-infected, tumor cells, preferably of the same type (the same tumor type).

In a particularly preferred embodiment, the sequence of steps a) to c) is repeated many times. By way of preference, new, in particular non-infected, dendritic cells, preferably of the same type, or new, in particular non-infected, tumor cells, preferably of the same type, are used for each repetition.

The sequence of steps a) to c) is preferably repeated once to 1000 times, particularly 10 times to 100 times, preferably 30 times to 60 times, wherein new, in particular non-infected, dendritic cells, preferably of the same type, or new, in particular non-infected, tumor cells, preferably of the same type, are used for each repetition.

By multiple repetition of steps a) to c), the arenavirus is constantly forced to adapt to a new environment, i.e. to new dendritic cells or tumor cells. This permanent adaptation pressure favors the occurrence of mutations, which can produce or improve the tumor-regressive properties of the arenavirus.

During the culturing of the arenavirus according to step b), a replication of the arenavirus genome and a propagation of the arenavirus occur within the dendritic cells or tumor cells.

The arenavirus according to step b) is preferably cultured under standard cell culture conditions.

The arenavirus is preferably cultured in the dendritic cells or tumor cells for a period of 1 minute to 1 year, in particular 10 hours to 1 month, preferably 24 hours to 72 hours.

The cultured arenavirus according to step c) is preferably isolated from a cell culture supernatant.

Preferably, the dendritic cells or tumor cells are sorted according to specific properties, preferably by means of a cell sorting device, and subsequently cultured, prior to isolating according to step c). The sorted cells are preferably cultured over a period of 24 hours.

In a preferred embodiment, the method further comprises the following steps:

d) cloning the isolated arenavirus and e) sequencing the isolated arenavirus.

With regard to further features and advantages of the method, in particular of the arenavirus and also the tumor, reference is made to the present description.

According to a fourth aspect, the invention relates to a method for producing an arenavirus with tumor-regressive, i.e. tumor-repelling/counteracting, properties or improved tumor-regressive properties.

The tumor is preferably a malignant tumor, preferably a carcinoma, melanoma, blastoma, lymphoma or sarcoma. Accordingly, the method is preferably a method for producing an arenavirus with (improved) carcinoma-, melanoma-, blastoma-, lymphoma- or sarcoma-regressive properties.

The method comprises the following steps:

a) infecting a host animal, which has a tumor, with an arenavirus, b) culturing the arenavirus in the infected host animal and c) isolating the cultured arenavirus or a subset of the cultured arenavirus from the infected host animal.

The sequence of steps a) to c) may also be referred to as a (single) passage of the arenavirus in the host animal.

In a preferred embodiment, tumor tissue is transplanted to the host animal prior to carrying out step a).

In an alternative embodiment, a genetically modified host animal is used which spontaneously develops the tumor.

Rodents in particular, preferably mice, can be used as host animals. For example, NOD SCID mice or LoxP-Tag mice can be used as host animals. In the Nod SCID mice, the SCID (Severe Combined Immunodeficiency) mutation is combined with a NOD (non-obese diabetic) type. In mice that are homozygous for the SCID mutation, no functional T-cells or B-cells are formed. By means of this immunodeficiency, these animals are exceptionally suitable for tolerating foreign body cells, for example transplanted tumors.

The host animal can be infected according to step a), for example by systemic, particularly intravenous, or local, for example subcutaneous, administration of the arenavirus.

In particular, the host animal can be infected by administration, preferably injection, of the arenavirus into the tumor of the host animal.

In a preferred embodiment, the sequence of steps a) to c) is repeated with a new, in particular non-infected, host animal, preferably of the same type.

In a particularly preferred embodiment, the sequence of steps a) to c) is repeated many times. A new, in particular non-infected host animal, preferably of the same type, is preferably used for each repetition. In other words, it is preferred according to the invention if the arenavirus is subjected to serial passage in host animals, preferably of the same type.

The sequence of steps a) to c) is preferably repeated once to 1000 times, particularly 10 times to 100 times, preferably 30 times to 60 times, wherein a new, in particular non-infected, host animal, preferably of the same type, is used for each repetition.

By multiple repetition of steps a) to c), the arenavirus is constantly forced to adapt to a new environment, i.e. to a new host animal. This permanent adaptation pressure favors the occurrence of mutations, which can produce or improve the tumor-regressive properties of the arenavirus.

During the culturing of the arenavirus according to step b), a replication of the arenavirus genome and a propagation of the arenavirus occur within the host animal.

The arenavirus is preferably cultured in the host animal for a period of 1 minute to 500 days, in particular 10 minutes to 100 days, preferably 1 hour to 30 days.

In a preferred embodiment, the arenavirus is isolated from urine, blood, the tumor, or organ lysates of the host animal.

In a further embodiment, the method further comprises the following steps:
d) infecting dendritic cells or tumor cells with the arenavirus isolated according to step c),
e) culturing the arenavirus in the infected dendritic cells or infected tumor cells and
f) isolating the cultured arenavirus or a subset of the cultured arenavirus from the infected dendritic cells or infected tumor cells.

The sequence of steps d) to f) may also be referred to as a (single) passage of the arenavirus in the dendritic cells or tumor cells.

The dendritic cells or tumor cells are infected according to step d) preferably by adding the arenavirus to the cells.

In a preferred embodiment, the sequence of steps d) to f) is repeated with new, in particular non-infected, dendritic cells, preferably of the same type, or with new, in particular non-infected, tumor cells, preferably of the same type (the same tumor type).

In a particularly preferred embodiment, the sequence of steps d) to f) is repeated many times. By way of preference, new, in particular non-infected, dendritic cells, preferably of the same type, or new, in particular non-infected, tumor cells, preferably of the same type, are used for each repetition. In other words, it is particularly preferred according to the invention if the arenavirus is additionally subjected to a serial passage in dendritic cells, preferably of the same type, or tumor cells, preferably of the same type.

The sequence of steps d) to f) is preferably repeated once to 1000 times, particularly 10 times to 100 times, preferably 30 times to 60 times, wherein new, in particular non-infected, dendritic cells, preferably of the same type, or new, in particular non-infected, tumor cells, preferably of the same type, are preferably used for each repetition.

The combination of a serial passage of the arenavirus in host animals, preferably of the same type, with a serial passage of the arenavirus in dendritic cells, preferably of the same type, or tumor cells, preferably of the same type, is suitable, because of the additionally increased adaptation pressure or mutation pressure in a particular manner, for producing arenaviruses with (improved) tumor-regressive properties.

The arenavirus is preferably cultured in the dendritic cells or tumor cells for a period of 1 minute to 500 days, in particular 10 minutes to 100 days, preferably 1 hour to 30 days.

Preferably, the dendritic cells or tumor cells are sorted according to specific properties, preferably by means of a cell sorting device, and subsequently cultured, prior to isolating according to step f). The sorted cells are preferably cultured over a period of 24 hours.

In a preferred embodiment, the method further comprises the following steps:
g) cloning the arenavirus isolated according to step f) and
h) sequencing the isolated arenavirus.

Alternatively, it can be provided according to the invention that the arenavirus isolated according to step c) is cloned and subsequently sequenced.

With regard to other features and advantages of the method, in particular the arenavirus, the tumor and also the dendritic cells and tumor cells, the present description is also fully incorporated by way of reference in order to avoid unnecessary repetitions.

Further features and advantages of the invention will emerge from the following description of preferred embodiments in the form of working examples, the associated figures and the claims. The embodiments described below are merely for the purpose of illustration and for the better understanding of the invention and are in no way to be understood as limiting.

BRIEF DESCRIPTION OF THE DRAWINGS

FIG. 13 shows effect of Candid #1 administration on tumor growth in HepG2 (hepatocellular carcinoma) tumor-bearing NOD.SCID mice.

FIG. 14 shows LCMV (MOI 1) replication results in primary hepatocytes, colon epithelial cells, and melanocytes) and in tumour cells from the same tissue source.

FIG. 15A shows the effect of LCMV administration on metastatic MOPC tumor growth in C57BL/6 mice.

FIG. 15B shows the effect of LCMV administration on survival in MOPC metastatic tumor-bearing C57BL/6 mice.

EXPERIMENTAL SECTION

1. Methods and Materials

1.1 Mice

Unless mentioned otherwise, the mice used were from a C57BL/6 background. $Map3k14^{aly/aly}$ mice lack NF-kB signals and are therefore highly immunosuppressed. $Irf3 \times Ir7^{-/-}$ mice cannot produce any interferon. NOD.SCID mice have no adaptive immune system. Therefore, it is possible to grow human tumors in these mice. LoxP-Tag mice spontaneously develop liver tumors.

1.2 Cell Lines and Reagents

MOPC cells are murine oropharynx carcinoma cells. Mc38 are murine colon carcinoma cells. Raw cells are immortalized macrophages. A431 are human lung carcinoma cells; Sw40 are human colon carcinoma cells, Hela are human cervical carcinoma cells. Primary macrophages were cultured from bone marrow precursor cells by means of M-CSF. Cells were maintained in Dulbecco's modified Eagle's medium with 10% fetal bovine serum (Sigma-Aldrich), 2 mmol/l L-glutamine and 100 U/ml penicillin. All cells were cultured in 5% CO2.

1.3 Viruses

The LCMV strain WE was obtained from the laboratory of Prof. Zinkernagel (Experimental Immunology, Zurich, Switzerland) and was propagated in L929 cells. Candid #1 was obtained from Professor Paula Cannon (University of Southern California).

1.4 Tumor Growth and Treatments

Approximately $5 \times 10^5$ tumor cells (in 100 microL) were injected subcutaneously into the right flank of 6 to 12 week old mice. The longest tumor diameter was measured by. Mice were treated by peritumoral injections of $2 \times 10^4$ PFU LCMV-WE or Candid #1 (in 100-200 microL).

1.5 Morphometric Analysis of Tumor Vessels

Morphometric analyses were performed with successive frozen sections, in which the endothelial cell marker CD31 was stained. Quantification of the microvessel density (MVD) was calculated using the mean of three tumor sections. MVD was calculated as the number of vessels per tumor area.

1.6 Detection of Hypoxia

Hypoxic tumor regions were detected by the formation of pimonidazole adducts after injection of pimonidazole into tumor-transplanted animals for 30 min. The tumor sections were stained using the Hypoxyprobe-1 Plus kit according to the manufacturer's instructions (Pharmacia Natur International, Inc.).

1.7 IFN-α ELISA

Serum IFN-α levels were determined by ELISA according to the manufacturer's data (Research Diagnostics RDI, Flanders, N.J.).

1.8 Statistical Analysis

The mean values were compared using an unpaired two-sided student t-test. The data are shown as mean±SEM. The level of statistical significance was set at $p<0.05$.

2. Investigations

2.1 Immortalized macrophages (tumour cells) and macrophages (primary) generated from primary bone marrow were infected with LCMV (WE strain). Replication was measured after 24 hours (n=3).

It could be shown that LCMV (WE strain) replicates both in immortalized and healthy cells. The results obtained are shown graphically in FIG. 1.

Figure 1:
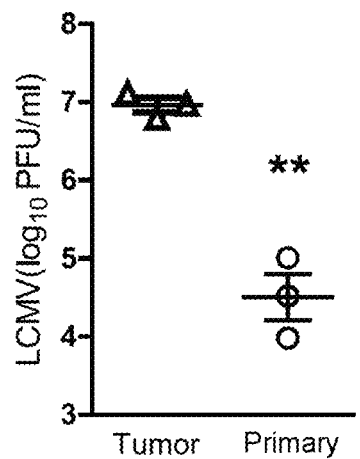
FIG. 1 shows LCMV (WE strain) replication results in immortalized macrophages ("tumour") and macrophages ("primary") generated from primary bone marrow.

FIG. 1 has the following legend:
Ordinate: LCMV ($\log_{10}$ PFU/ml)
Abscissa: Tumor cells/healthy macrophages (primary)

2.2 WT C57BL/6 mice were treated with $5 \times 10^5$ MOPC cells (day 3). One group of mice was additionally treated peritumorally with $2 \times 10^4$ PFU LCMV (WE strain) (day 0). Tumor growth was observed.

It could be shown that the treatment with LCMV caused almost complete tumor regression. The results obtained are shown graphically in FIG. 2.

Figure 2:
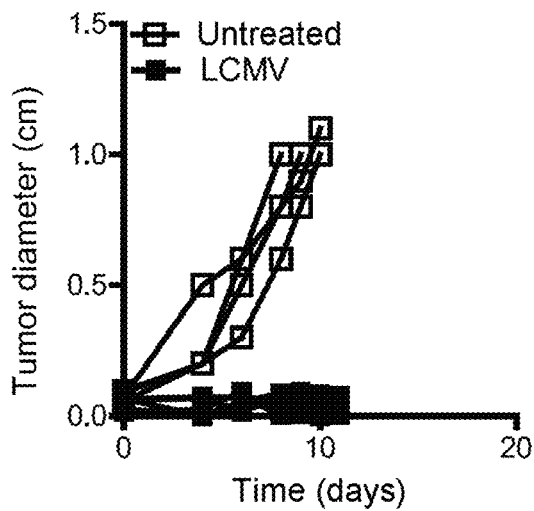
FIG. 2 shows the effect of LCMV (WE strain) administration on MOPC (mouse plasmacytoma cell) tumor growth in C57BL/6 mice.

FIG. 2 has the following legend:
Ordinate: Tumor diameter (cm)
Abscissa: Time (days)

2.3 WT C57BL/6 mice were treated with $5 \times 10^5$ MC38 cells (day 3). One group of mice was additionally treated peritumorally with $2 \times 10^4$ PFU LCMV (WE strain) (day 0). Tumor growth was observed.

It could be shown that the treatment with LCMV caused a significant tumor regression. The results obtained are shown graphically in FIG. 3.

Figure 3:
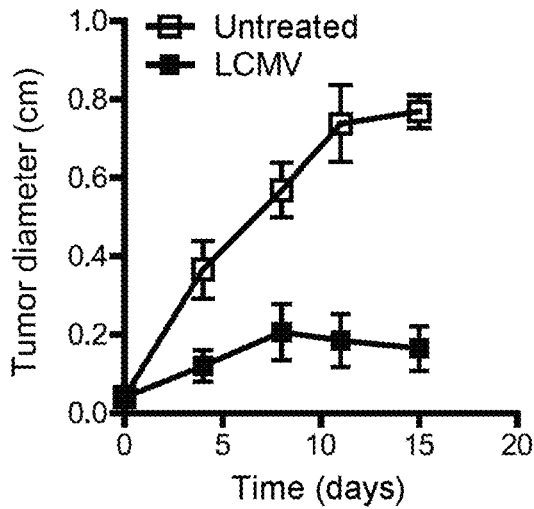
FIG. 3 shows the effect of LCMV (WE strain) administration on MC38 (mouse colon adenocarcinoma cell) tumor growth in C57BL/6 mice.

FIG. 3 has the following legend:
Ordinate: Tumor diameter (cm)
Abscissa: Time (days)

2.4 About nine month old LoxP-TAg mice with spontaneously developed liver carcinomas were infected intravenously with $2 \times 10^6$ PFU LCMV or left untreated. The tumor nodes (diameters>=3 mm) were quantified macroscopically on day 6 (n=3) and day 20 (n=4-5).

It could be shown that the treatment with LCMV significantly reduced the number of carcinomatous liver nodes. The results obtained are shown graphically in FIG. 4.

Figure 4:
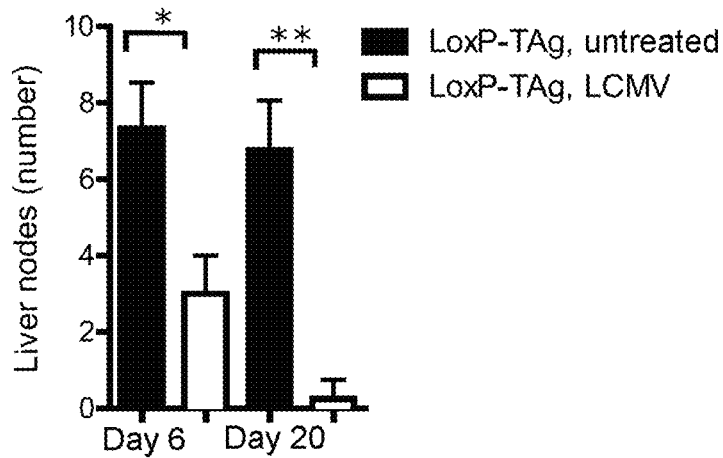
FIG. 4 shows the effect of LCMV (WE strain) administration on spontaneous liver carcinoma tumor growth in LoxP-TAg mice.

FIG. 4 has the following legend:
Ordinate: Liver nodes (number)
Abscissa: Time 2.5 WT C57BL/6 mice (n=4/group) were injected subcutaneously with 5×10⁵ MOPC cells (day −3) or LCMV (WE strain) 2×10⁴ PFU (day 0) or both 5×10⁵ MOPC cells (day −3) and 2×10⁴ PFU LCMV (day 0). Serum samples were collected on day 3 and an IFN-α-ELISA was performed.

It could be shown that the LCMV caused a drastically increased secretion of interferon-γ in experimental animals which were simultaneously administered carcinoma cells. The results obtained are shown graphically in FIG. 5.

Figure 5:
FIG. 5 shows the effect of LCMV (WE strain) on interferon-γ secretion in MOPC tumor-bearing C57BL/6 mice.

FIG. 5 has the following legend:
Ordinate: IFN-α (pg/ml)

2.6 Map3k14$^{aly/aly}$ mice and WT mice were treated with 5×10⁵ MOPC cells (day 3). One group of mice was additionally treated peritumorally with 2×10⁴ PFU LCMV (WE strain) (day 0). Tumor growth was observed.

It could be shown that the treatment with LCMV caused tumor regression. The results obtained are shown graphically in FIG. 6.

Figure 6:
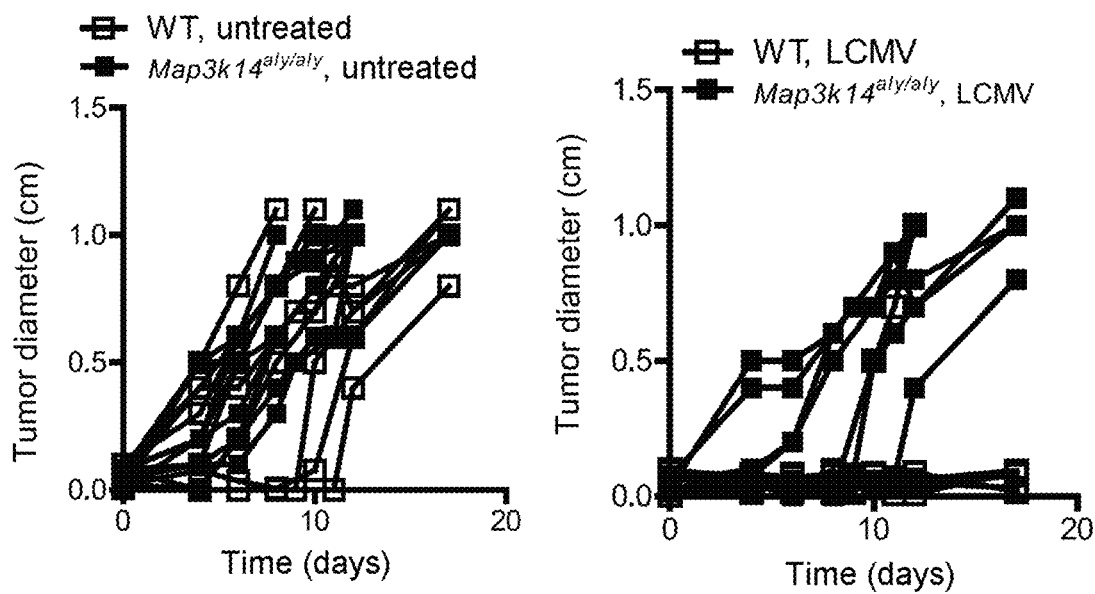
FIG. 6 shows the effect of LCMV (WE strain) administration on MOPC tumor growth in Map3k14$^{aly/aly}$ mice compared to corresponding wild type mice.

FIG. 6 has the following legend:
Ordinate: Tumor diameter (cm)
Abscissa: Time (days)

2.7 Irf3×Ir7$^{−/−}$ mice and WT mice were treated with 5×10⁵ MOPC cells (day 3). One group of mice was additionally treated peritumorally with 2×10⁴ PFU LCMV (WE strain) (day 0). Tumor growth was observed.

It could be shown that the treatment with LCMV caused tumor regression. The results obtained are shown graphically in FIG. 7.

Figure 7:
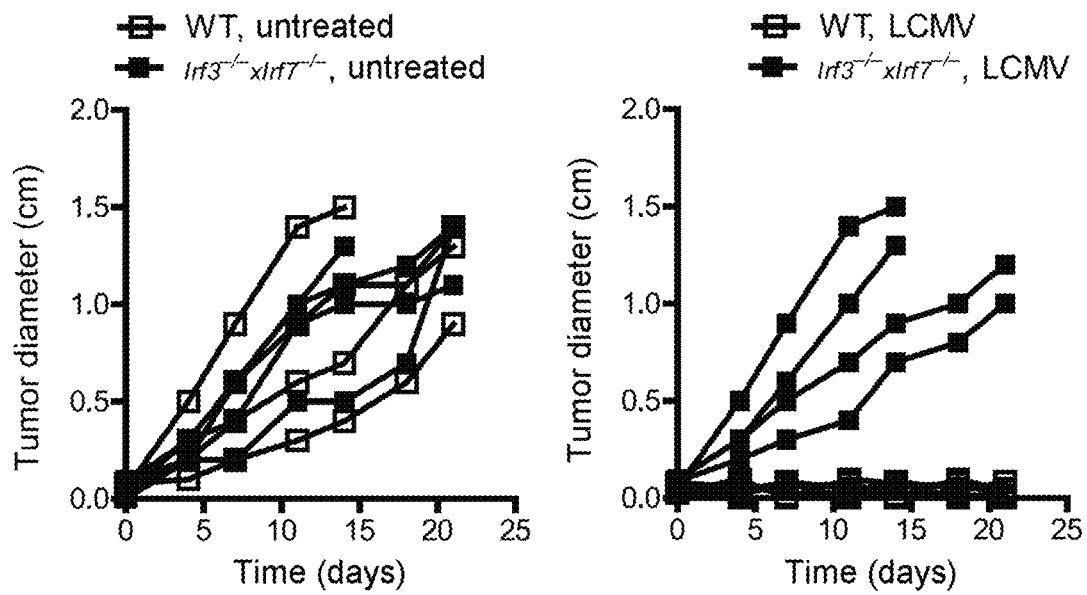
FIG. 7 shows the effect of LCMV (WE strain) administration on MOPC tumor growth in Irf3×Ir7$^{-/-}$ mice compared to corresponding wild type mice.

FIG. 7 has the following legend:
Ordinate: Tumor diameter (cm)
Abscissa: Time (days)

2.8 WT mice were treated with 5×10⁵ MOPC cells (day 3). One group of mice was additionally treated peritumorally with 2×10⁴ PFU LCMV (WE strain) (day 0). On day 9 after the tumor graft, the tumors were analyzed histologically with CD31 staining. The microvessel density (MDV) and the vessel-vessel spacing were quantified.

It could be shown that the treatment with LCMV caused a decrease in tumor vessel density. The results obtained are shown graphically in FIG. 8A.

Figure 8A:
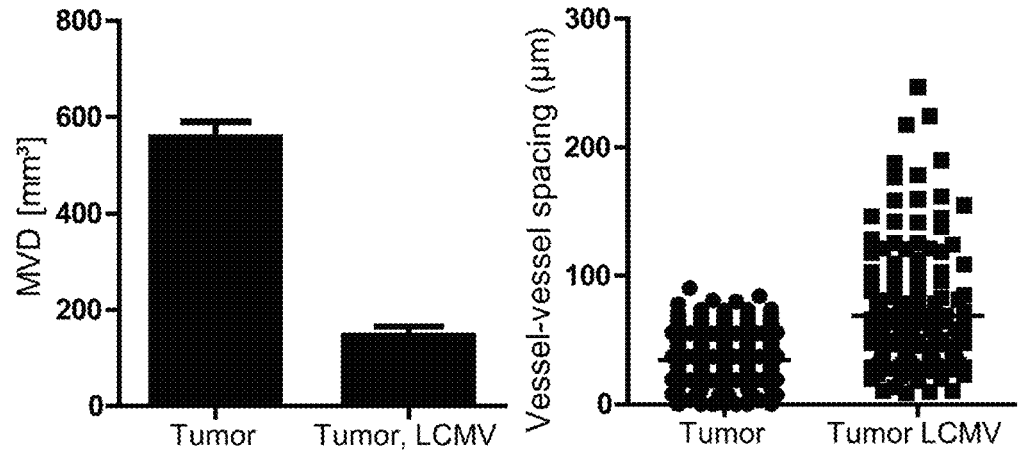
FIG. 8A shows effect of LCMV (WE strain) administration on tumor microvessel density (MDV) and vessel-vessel spacing in MOPC tumor-bearing wild type mice.

FIG. 8A has the following legends:

| Left side: | Right side: |
|---|---|
| Ordinate: MVD [mm³] | Ordinate: Vessel-vessel spacing (μm) |
| Abscissa: Tumor/Tumor LCMV | Abscissa: Tumor/Tumor LCMV |

2.9 WT mice were treated with 5×10⁵ MOPC cells (day 3). One group of mice was additionally treated peritumorally with 2×10⁴ PFU LCMV (WE strain) (day 0). On day 9, the animals were injected with pimonidazole, and the tumors were then analyzed histologically for hypoxic regions.

It could be shown that the treatment with LCMV caused oxygen deficiency in the carcinoma tissue. The results obtained are shown graphically in FIG. 8B.

Figure 8B:
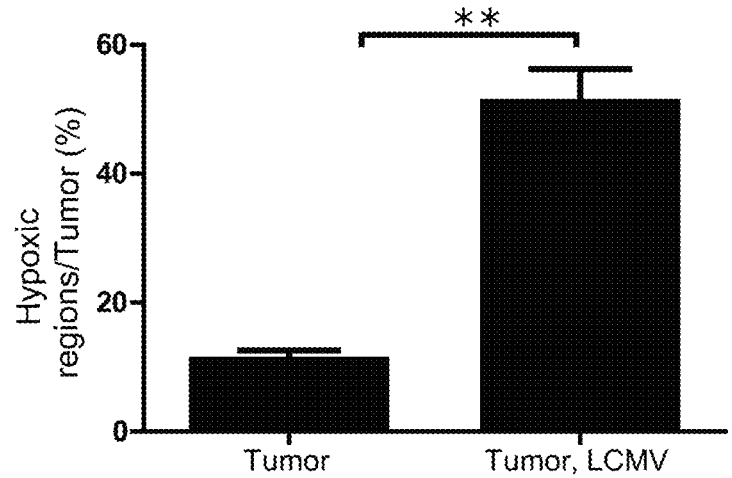
FIG. 8B shows effect of LCMV (WE strain) administration on tumor hypoxic regions in MOPC tumor-bearing wild type mice.

FIG. 8B has the following legend:
Ordinate: Hypoxic regions/tumor (%)
Abscissa: Tumor/Tumor LCMV 2.10 WT C57BL/6 mice were injected subcutaneously with 5×10⁵ MOPC cells in the right flank (day 3). On day 0, a group of animals were treated with 2×10⁴ PFU LCMV (WE strain) in the right flank (ipsilateral), left flank (contralateral) or intravenously. Tumor growth was observed.

It could be shown that the treatment with LCMV caused tumor regression even with systemic administration. The results obtained are shown graphically in FIG. 9.

Figure 9:
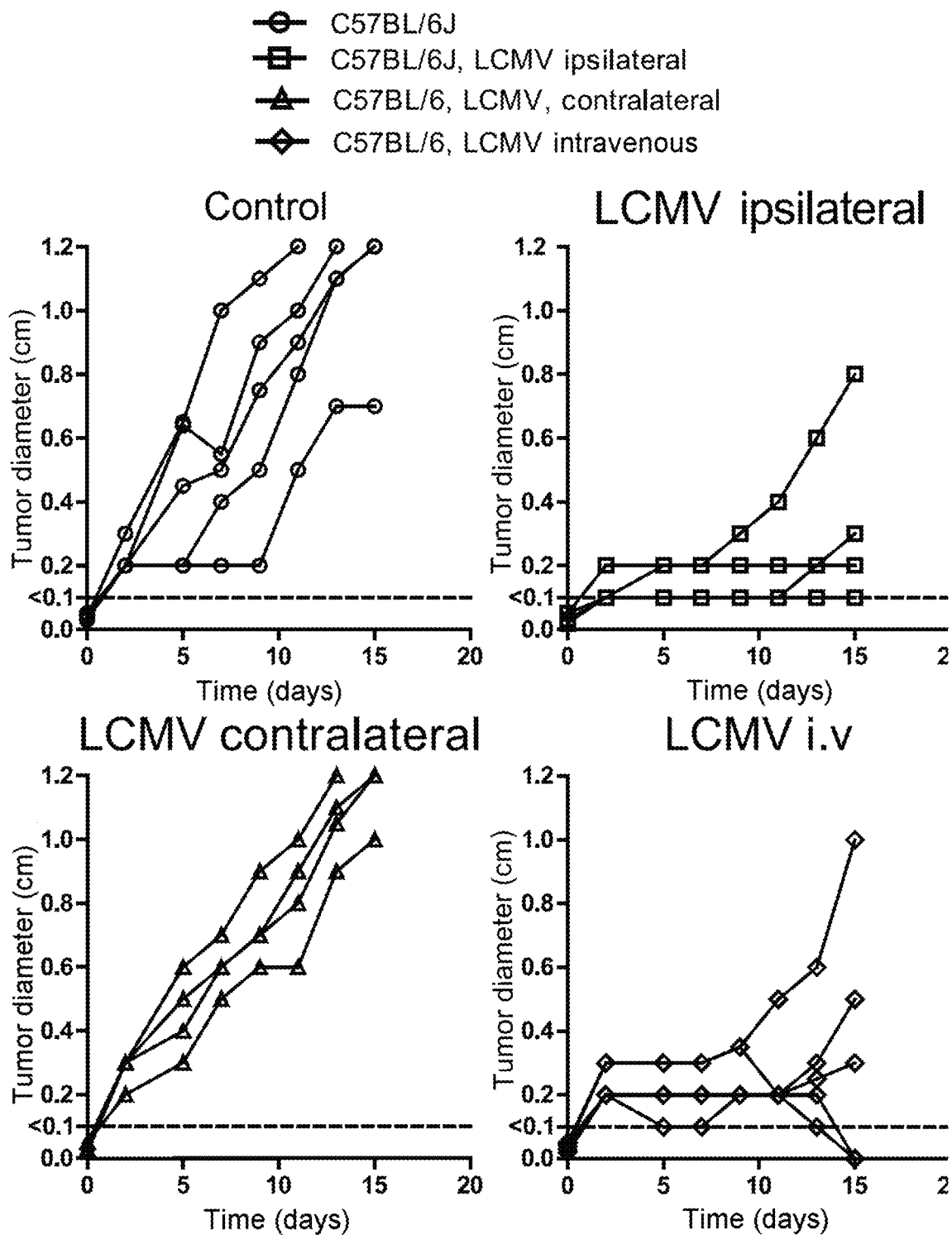
FIG. 9 shows the effect of LCMV (WE strain) administration (ipsilateral, contralateral, and intravenous) on MOPC tumor growth in C57BL/6 mice.

FIG. 9 has the following legend:
Ordinate: Tumor diameter (cm)
Abscissa: Time (days)

2.11 NOD.SCID mice were injected subcutaneously with 5×10⁵ A431 cells (day −3) and then either left untreated or treated with 2×10⁴ PFU LCMV (WE strain). The tumor size (longest diameter) was measured on the specified day. The mice were sacrificed when the tumor size reached 12 mm.

It could be shown that the treatment with LCMV increased the survival rate in the experimental animals. The results obtained are shown graphically in FIG. 10.

Figure 10:
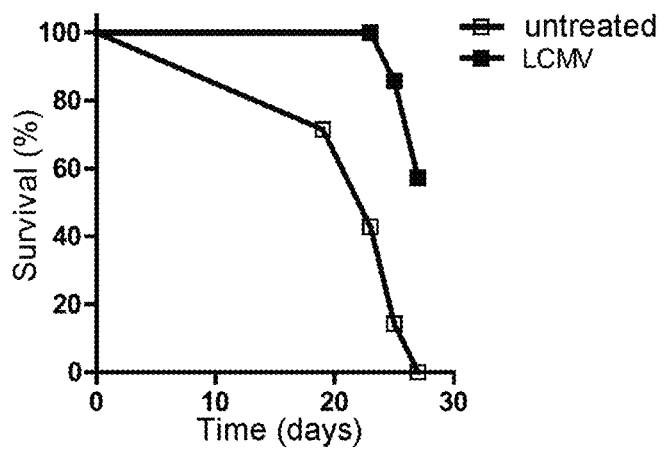
FIG. 10 shows effect of LCMV (WE strain) administration on survival in A431 (squamous carcinoma) tumor-bearing NOD.SCID mice.

FIG. 10 has the following legend:
Ordinate: Survival (%)
Abscissa: Time (days)

2.12 NOD.SCID mice were treated with 5×10⁵ Sw40 cells (day 0). A group of mice was additionally treated peritumorally with 2×10⁴ PFU LCMV (WE strain) or 2×10⁴ PFU Candid #1 (day 0). Tumor growth was observed.

It could be shown that the treatment with LCMV and Candid #1 caused tumor regression. The results obtained are shown graphically in FIG. 11.

Figure 11:
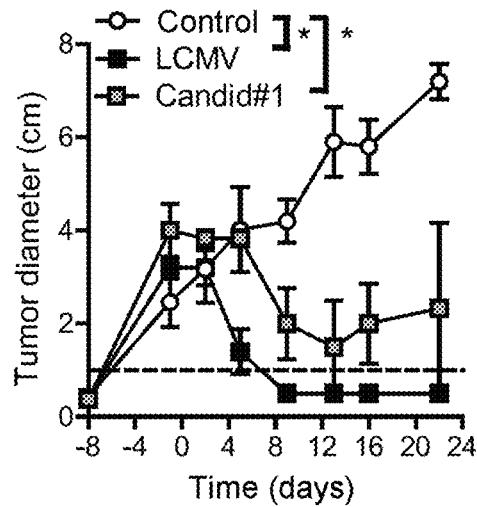
FIG. 11 shows effect of LCMV (WE strain) administration on tumor growth in A431 (colon adenocarcinoma) tumor-bearing NOD.SCID mice.

FIG. 11 has the following legend:
Ordinate: Tumor diameter (cm)
Abscissa: Time (days)

2.13 NOD.SCID mice were treated with 5×10⁵ Hela cells (day 0). A group of mice was additionally treated peritumorally with 2×10⁴ PFU LCMV (WE strain) (day 3). Tumor growth was observed.

It could be shown that the treatment with LCMV caused tumor regression. The results obtained are shown graphically in FIG. 12.

Figure 12:
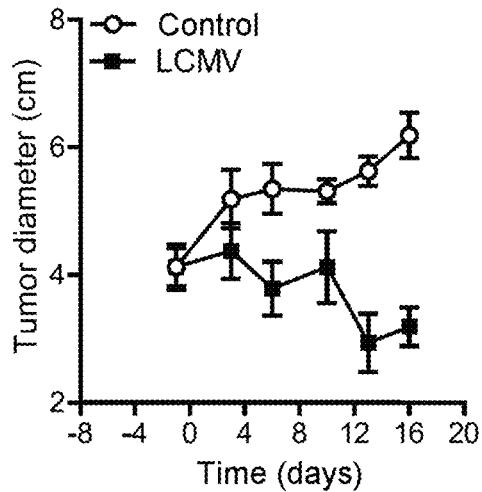
FIG. 12 shows effect of Candid #1 administration on tumor growth in HeLa cell-bearing NOD.SCID mice.

FIG. 12 has the following legend:
Ordinate: Tumor diameter (cm)
Abscissa: Time (days)

2.14 NOD.SCID mice were treated with 5×10⁵ HepG2 cells (day 10) and then additionally treated peritumorally with or without 2×10⁴ PFU Candid #1 (day 0). Tumor growth was observed.

It could be shown that the treatment with Candid #1 caused tumor regression with this tumor type. The results obtained are shown graphically in FIG. 13.

FIG. 13 has the following legend:
Ordinate: Tumor diameter (cm)
Abscissa: Time (days)

2.15 Primary human cells (hepatocytes, colon epithelial cells, melanocytes) and tumour cells from the same tissue source were infected with LCMV (MOI 1). The amount of virus was measured in the supernatant after 1, 2 and 3 days.

In this experiment it was shown that arenaviruses are replicated in tumor cells in comparison to healthy tissue.

FIG. 14 has the following legend:
Ordinate: Infectious virus in cell culture supernatant (logarithmic plaque forming units)
Abscissa: Time (days)

2.16 Tumor diameter (A) and survival (B) of C57BL/6 mice bearing a metastasis in the shoulder and a metastasis in the flank (MOPC cells), which were left untreated or had been treated intravenously with $2 \times 10^6$ PFU LCMV.

It could be shown in this experiment that intravenous therapy of LCMV acts very efficiently on two local metastases and thus prolongs survival.

FIG. 15A has the following legend:
Ordinate: Tumor diameter of both metastases (cm)
Abscissa: Time (days)

FIG. 15B has the following legend:
Ordinate: Survival in percent
Abscissa: Time (days)

2.17 Tumor diameter of C57BL/6 mice bearing a melanoma (B16F10 cells) which were left untreated or were treated intratumorally with $2 \times 10^4$ PFU LCMV.

It could be shown in this experiment that local therapy with LCMV is very efficient in melanoma.

Figure 16:
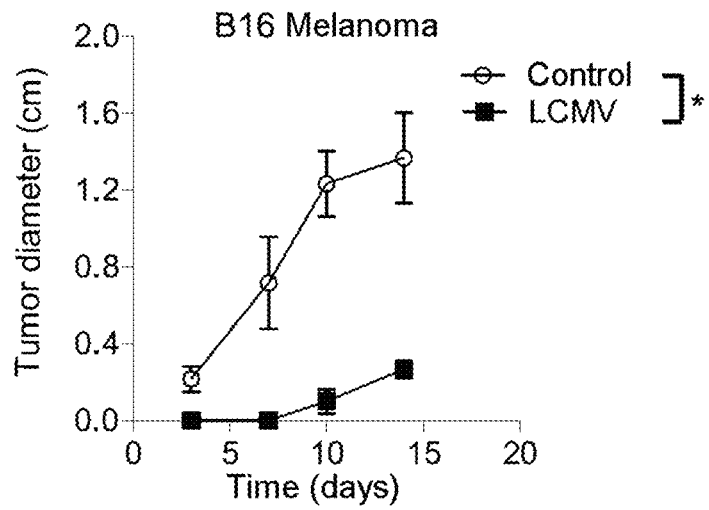
FIG. 16 shows the effect of LCMV administration on B16F10 (melanoma) tumor growth in C57BL/6 mice.

FIG. 16 has the following legend:
Ordinate: Tumor diameter of the melanoma (cm)
Abscissa: Time (days)

2.18 Number of melanomas of MT/ret mice (develop endogenous melanomas), which were left untreated or were treated intravenously with $2 \times 10^6$ PFU LCMV.

It could be shown in this experiment that systemic therapy with LCMV is very efficient in melanoma.

Figure 17:
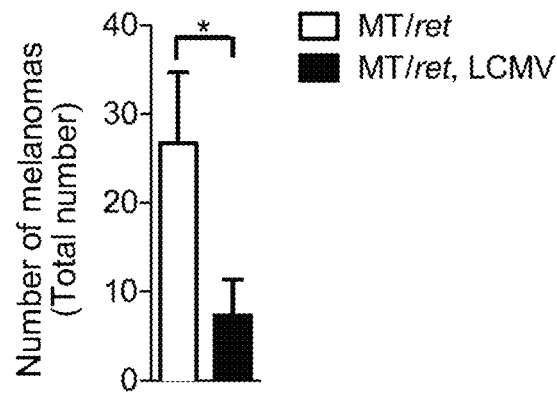
FIG. 17 shows the effect of LCMV administration on spontaneous melanoma tumor growth in MT/ret mice.

FIG. 17 has the following legend:
Ordinate: Number of melanomas 2.19 Tumor diameter (A) and survival (B) of NOD.SCID mice bearing a human fibrosarcoma (Sw872 cells), which were left untreated or were treated intratumorally with $2 \times 10^6$ PFU Candid #1.

It could be shown in this experiment that Candid #1 acts very efficiently also in the case of fibrosarcoma and thus prolongs survival.

Figure 18A:
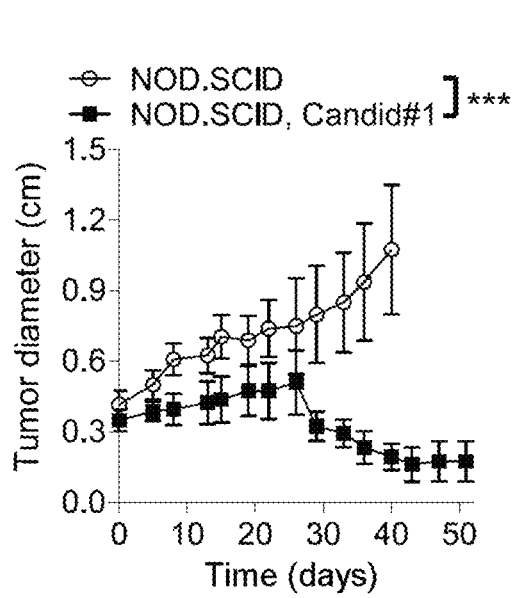
FIG. 18A shows the effect of LCMV administration on Sw872 (fibrosarcoma) tumor growth in NOD.SCID mice.

FIG. 18A has the following legend:
Ordinate: Tumor diameter (cm)
Abscissa: Time (days)

Figure 18B:
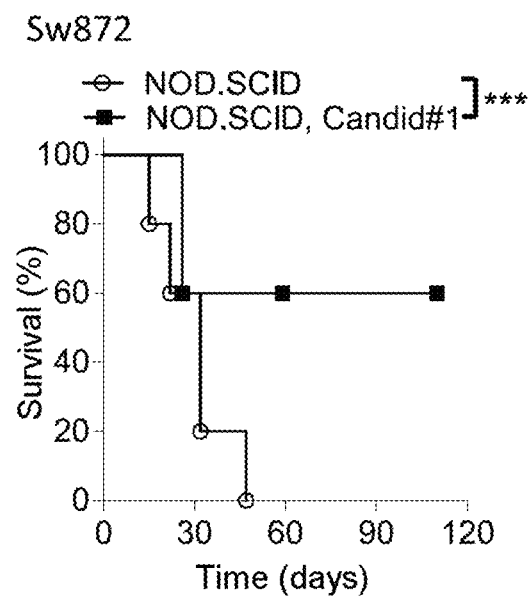
FIG. 18B shows the effect of LCMV administration on survival in Sw872 (fibrosarcoma) tumor-bearing NOD.SCID mice.

FIG. 18B has the following legend:
Ordinate: Survival in percent
Abscissa: Time (days)

2.20 Tumor diameter (A) and survival (B) of NOD.SCID mice bearing a human pharyngeal carcinoma (FaDu cells), which were left untreated or were treated intratumorally with $2 \times 10^6$ PFU LCMV.

It could be shown in this experiment that LCMV acts very efficiently also in the case of pharyngeal carcinoma and thus prolongs survival.

Figures 19A, 19B:
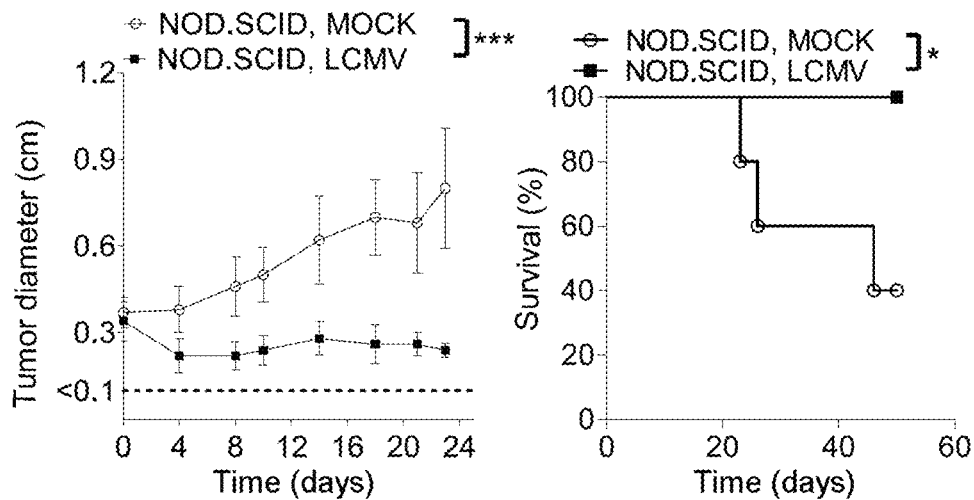
FIG. 19A shows the effect of LCMV administration on FaDu (pharyngeal carcinoma) tumor growth in NOD.SCID mice.
FIG. 19B shows the effect of LCMV administration on survival in FaDu (pharyngeal carcinoma) tumor-bearing NOD.SCID mice.

FIG. 19A has the following legend:
Ordinate: Tumor diameter (cm)
Abscissa: Time (days)

FIG. 19B has the following legend:
Ordinate: Survival in percent
Abscissa: Time (days)

2.21 Expression of receptors on tumor-specific T cells (PD-1, IL2 receptor, IL7 receptor), which influence the function of T cells. Tumor-specific T cells are derived from the blood of mice with B16F10 tumors, which were additionally treated intratumorally with or without LCMV.

It could be shown in this experiment that LCMV positively influences the tumor-specific T cells.

Figure 20:
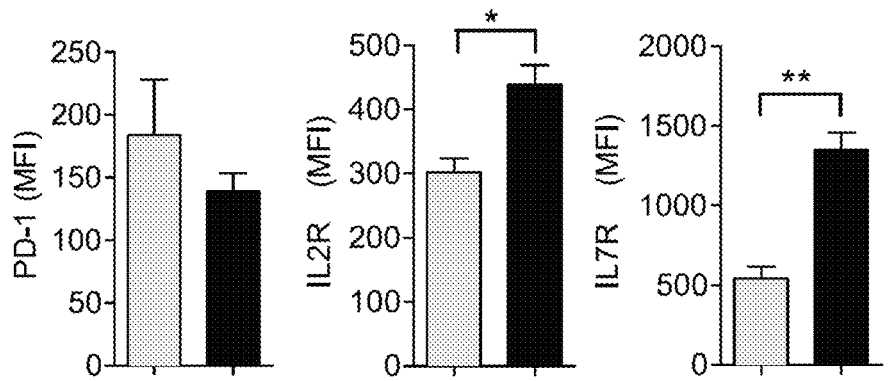
FIG. 20 shows the effect of LCMV on T-cell expression of PD-1, IL2 receptor, and IL7 receptor in B16F10 tumor-bearing mice.

FIG. 20 has the following legend:
Ordinate: Potency of the expression of the different receptors (mean fluorescence intensity)

2.22 Tumor diameter (A) and survival (B) of C57BL/6 mice bearing a murine subcutaneous lymphoma (EL4 cells) which were treated with or without tumor-specific T cells (OT1 cells) and additionally intratumorally with or without LCMV ($2 \times 10^6$ PFU).

It could be shown in this experiment that LCMV acts synergistically with T cell therapy.

Figures 21A, 21B:
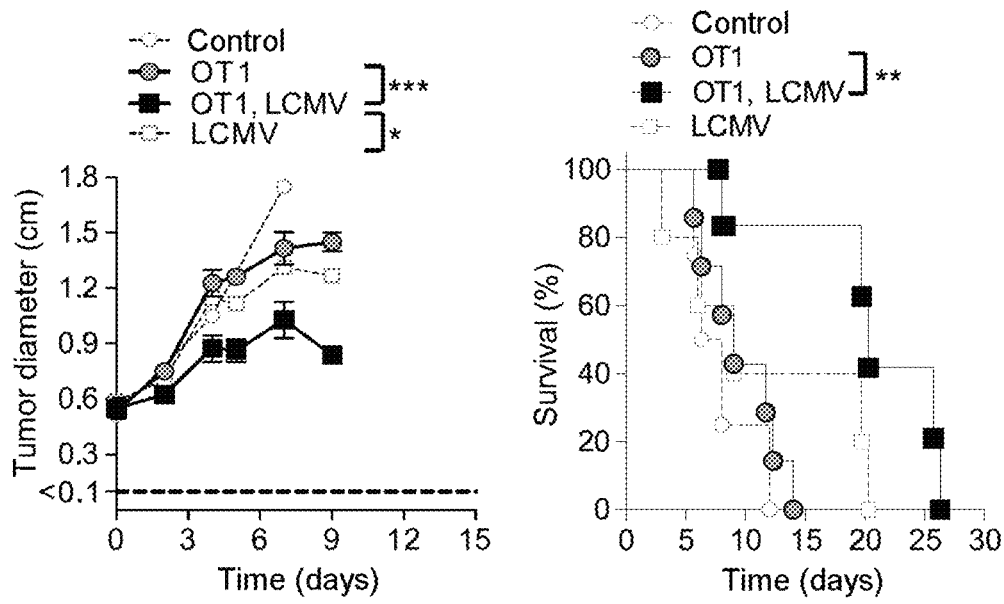
FIG. 21A shows the effect of LCMV administration on EL4 (lymphoma) tumor growth in C57BL/6 mice.
FIG. 21B shows the effect of LCMV administration on survival in EL4 (lymphoma) tumor-bearing C57BL/6 mice.

FIG. 21A has the following legend:
Ordinate: Tumor diameter (cm)
Abscissa: Time (days)

FIG. 21B has the following legend:
Ordinate: Survival in percent
Abscissa: Time (days)

2.23 Survival of C57BL/6 mice and PD-1 deficient mice (Pdcd1$^{-/-}$ mice) bearing a murine pharyngeal carcinoma (MOPC cells) and which were treated intratumorally with LCMV ($2 \times 10^4$ PFU).

It could be shown in this experiment that LCMV acts synergistically with a PD-1 blockade.

Figure 22:
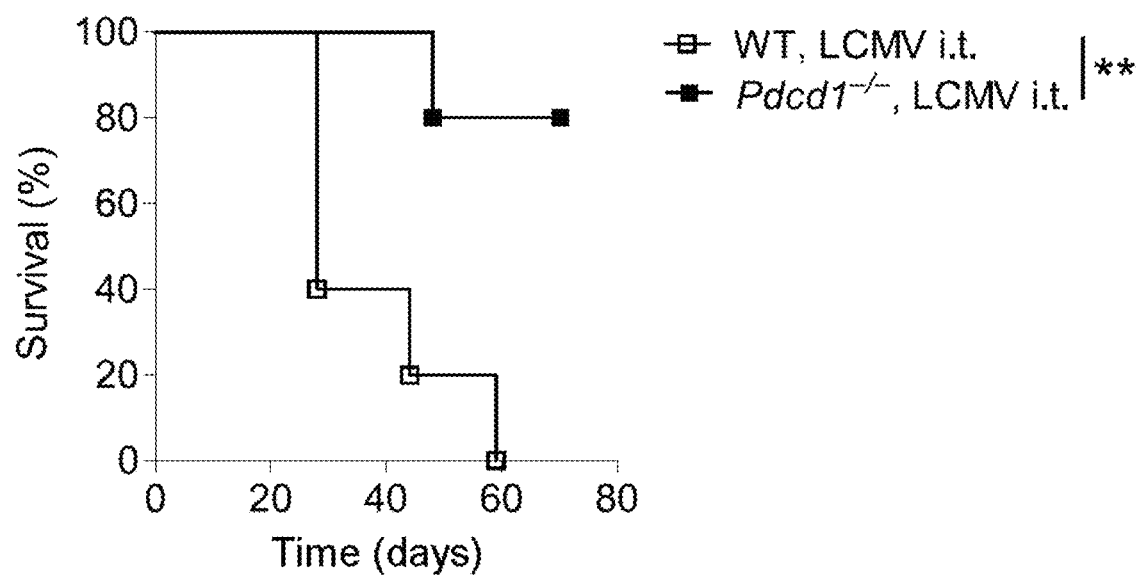
FIG. 22 shows the effect of LCMV administration on survival in MOPC tumor-bearing C57BL/6 and $Pdcd1^{-/-}$ mice.

FIG. 22 has the following legend:
Ordinate: Survival in percent
Abscissa: Time (days)

The nucleic acid sequences SEQ ID No. 1 to SEQ ID No. 6 mentioned in the general description correspond to the nucleic acid sequences disclosed in the following sequence listing.

The invention claimed is:

1. A method of enhancing an innate immune response in a subject bearing a malignant tumor, comprising:

administering to the subject a lymphocytic choriomeningitis virus (LCMV) that increases secretion of interferon-$\alpha$ by innate (congenital) immune cells, thereby activating the innate (congenital) immune cells, wherein the sequences of the L- and S-ribonucleic acids of the LCMV are selected from the group consisting of WE, Clone 13 and Docile L- and S-ribonucleic acid sequences.

2. The method of claim 1, wherein the LCMV has been subjected to serial passage in a tumor cell line of the same type as the tumor prior to the administering step.

3. The method of claim 1, wherein the tumor is selected from the group consisting of carcinoma, melanoma, blastoma, lymphoma, and sarcoma.

4. The method of claim 1, wherein the LCMV comprises an S-ribonucleic acid sequence according to SEQ ID No. 5 or ambisense sequence thereof, or an L-ribonucleic acid sequence according to SEQ ID No. 6 or ambisense sequence thereof.

5. The method of claim 1, wherein the L- and S-ribonucleic acids of the LCMV are WE L- and S-ribonucleic acids.

6. The method of claim 1, wherein the subject is a human.

7. A method according to claim 1, wherein the tumor is a solid tumor.

8. The method of claim 7, wherein the LCMV has been subjected to serial passage in a tumor cell line of the same type as the tumor prior to the administering step.

9. The method of claim 7, wherein the tumor is carcinoma.

10. The method of claim 7, wherein the tumor is melanoma.

11. The method of claim 7, wherein the LCMV comprises an S-ribonucleic acid sequence according to SEQ ID No. 5 or ambisense sequence thereof, or an L-ribonucleic acid sequence according to SEQ ID No. 6 or ambisense sequence thereof.

12. The method of claim 7, wherein the L- and S-ribonucleic acids of the LCMV are WE L- and S-ribonucleic acids.

13. The method of claim 7, wherein the subject is a human.

* * * * *